(12) United States Patent
Witelson

(10) Patent No.: US 11,149,459 B2
(45) Date of Patent: *Oct. 19, 2021

(54) POOL CLEANING ROBOT WITH REMOVABLE FILTER AND IMPELLER

(71) Applicant: Maytronics Ltd., Kibutz Yizrael (IL)

(72) Inventor: Shay Witelson, Kibbutz Yizrael (IL)

(73) Assignee: Maytronics Ltd., Kibutz Yizrael (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,254

(22) Filed: Feb. 11, 2021

(65) Prior Publication Data

US 2021/0164253 A1     Jun. 3, 2021

Related U.S. Application Data

(63) Continuation of application No. 16/375,030, filed on Apr. 4, 2019, now Pat. No. 10,920,440, which is a
(Continued)

(51) Int. Cl.

| | |
|---|---|
| *E04H 4/16* | (2006.01) |
| *C02F 1/00* | (2006.01) |
| *H02J 50/00* | (2016.01) |
| *B60L 1/00* | (2006.01) |
| *H02J 7/02* | (2016.01) |
| *H02K 7/18* | (2006.01) |
| *B60L 50/52* | (2019.01) |

(Continued)

(52) U.S. Cl.
CPC .............. *E04H 4/1672* (2013.01); *A61L 2/10* (2013.01); *B25J 11/00* (2013.01); *B60L 1/003* (2013.01); *B60L 50/52* (2019.02); *C02F 1/001* (2013.01); *E04H 4/1654* (2013.01); *G05D 1/021* (2013.01); *H02J 7/02* (2013.01); *H02J 7/025* (2013.01); *H02J 50/00* (2016.02); *H02K 7/1823* (2013.01); *B60L 2240/62* (2013.01); *B60L 2260/32* (2013.01); *C02F 2103/42* (2013.01); *H02J 50/10* (2016.02); *Y02T 10/64* (2013.01); *Y02T 10/70* (2013.01); *Y02T 10/7072* (2013.01); *Y02T 10/72* (2013.01); *Y02T 90/14* (2013.01); *Y02T 90/16* (2013.01); *Y10S 901/01* (2013.01)

(58) Field of Classification Search
CPC ..... E04H 4/1672; E04H 4/1654; B60L 53/14; B60L 50/52; B60L 1/003; A61L 2/10; B25J 11/00; C02F 1/001; G05D 1/021; H02J 7/02; H02J 7/025; H02J 50/00; H02K 7/1823
USPC .......................................................... 210/780
See application file for complete search history.

(56) References Cited

U.S. PATENT DOCUMENTS

| | | | |
|---|---|---|---|
| 10,920,440 B2 * | 2/2021 | Witelson | ............... E04H 4/1654 |
| 2010/0065482 A1 * | 3/2010 | Sumonthee | ........... E04H 4/1654 |
| | | | 210/167.1 |
| 2013/0152317 A1 | 6/2013 | Erlich et al. | |

* cited by examiner

*Primary Examiner* — Claire A Norris
(74) *Attorney, Agent, or Firm* — Reches Patent

(57) ABSTRACT

A pool cleaning robot that may include a drive motor; an impeller; an impeller motor that is configured to rotate the impeller; wherein the impeller, once rotated at a first rotational direction, is configured to induce fluid to flow through the pool cleaning robot; a filter for filtering fluid that flows through the pool cleaning robot; and wherein the filter and the impeller are detachably coupled to one or more elements of the pool cleaning robot; and are configured to concurrently exit the pool cleaning robot while the impeller motor remains coupled to the one or more elements of the pool cleaning robot.

20 Claims, 40 Drawing Sheets

Related U.S. Application Data continuation of application No. 15/912,590, filed on Mar. 6, 2018, now Pat. No. 10,407,933, which is a continuation of application No. 14/433,859, filed as application No. PCT/IL2013/051055 on Dec. 22, 2013, now Pat. No. 9,903,131.

(60) Provisional application No. 61/745,556, filed on Dec. 22, 2012.

(51) Int. Cl.
*A61L 2/10* (2006.01)
*B25J 11/00* (2006.01)
*G05D 1/02* (2020.01)
*H02J 50/10* (2016.01)
*C02F 103/42* (2006.01)

Performing, by at least one of a pool cleaning robot and an underwater station, in an autonomous manner at least one out of pool cleaning robot filter replacement and pool cleaning robot charging. 410

Filtering fluid by a pool cleaning robot by using a filter that fulfils at least one of the following: (i) it has a filter core that is rotated by a filter core rotator when the filter applied a filtering operation, (ii) is positioned in a filtering position while at least one other filter of the pool cleaning robot is positioned within the pool cleaning robot in a non-filtering position, (iii) is positioned in a filtering position when the pool cleaning robot and by a filter manipulator. 510

POOL CLEANING ROBOT WITH REMOVABLE FILTER AND IMPELLER

RELATED APPLICATIONS

This application is a continuation of U.S. patent application Ser. No. 16/375,030 filing date Apr. 4, 2019, which is a continuation of U.S. patent application Ser. No. 15/912,590 filing date Mar. 6, 2018, which is a continuation of U.S. patent application Ser. No. 14/433,859 filing date Apr. 7, 2015 which is a national phase application of PCT patent application serial number PCT/IL2013/051055 international filing date Dec. 22, 2013 which claims priority from U.S. provisional patent Ser. No. 61/745,556 filing date Dec. 22, 2012, all being incorporated herein by reference.

FIELD OF THE INVENTION

This invention relates to pool cleaning robots, and particularly to autonomous pool cleaning robots.

BACKGROUND OF THE INVENTION

Pool cleaning robots are adapted for use for cleaning a pool while being connected to electrical power cables or to a hose of a suction system. The hose and/or power cable can get tangled and may temporarily limit the usage of the pool.

Once a filter of a pool cleaning robot is clogged the pool cleaning robot is manually taken out of the pool and its filter can be washed by a user of the pool cleaning robot.

Taking a pool cleaning robot out of the pool is a time and effort consuming operation that is not very fond by the users. In many cases the users delay these manual operations or even skip them causing the pool cleaning robot to operate in a sub-optimal manner.

There is a growing need to provide autonomous robots that require a lesser amount of human intervention in their maintenance.

SUMMARY OF THE INVENTION

There may be provided a pool cleaning robot and a method as substantially illustrated in the specification and/or claims and/or drawings.

BRIEF DESCRIPTION OF THE DRAWINGS

In order to understand the invention and to see how it may be carried out in practice, an embodiment will now be described, by way of a non-limiting example only, with reference to the accompanying drawings, in which:

FIG. 21 illustrates a method according to an embodiment of the invention; and

FIG. 22 illustrates a method according to an embodiment of the invention.

DETAILED DESCRIPTION OF EMBODIMENTS

According to various embodiments of the invention there is provided a pool cleaning robot that is autonomous.

The pool cleaning robot can be being charged while being underwater.

Contactless Underwater Charging of a Pool Cleaning Robot

Figure 1:
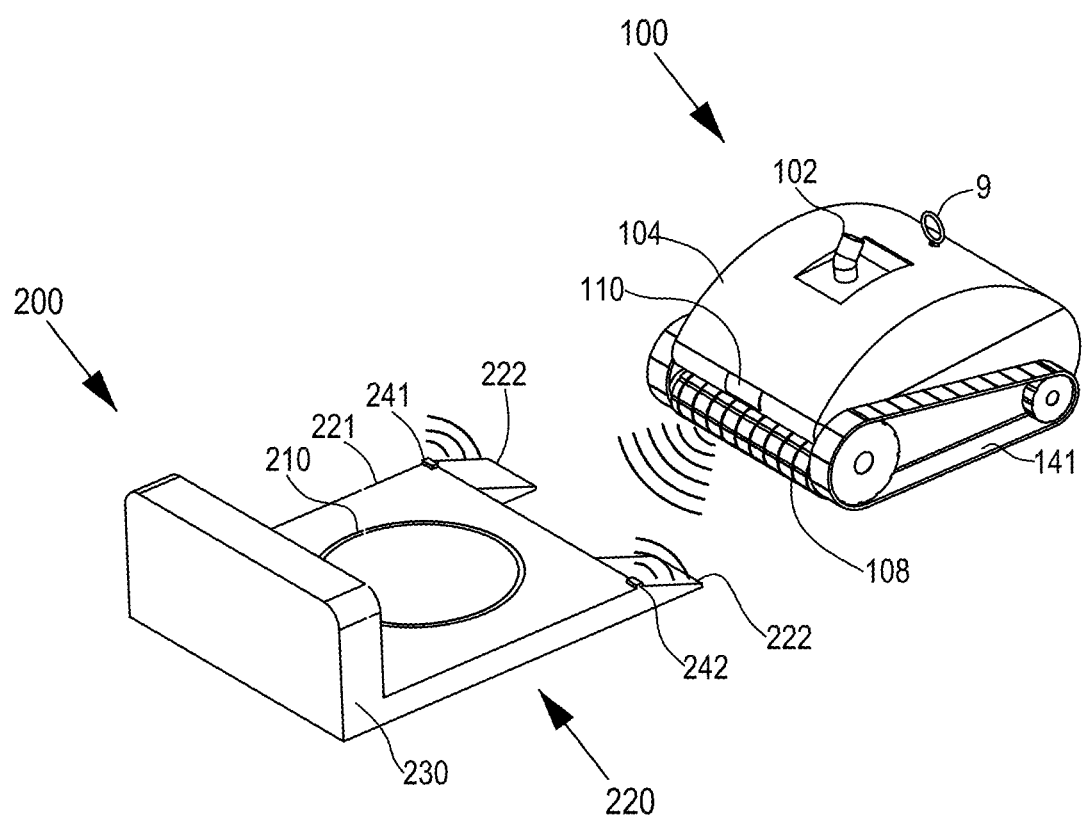
FIG. 1 illustrates a pool cleaning robot and an underwater station according to an embodiment of the invention.
Figure 3A:
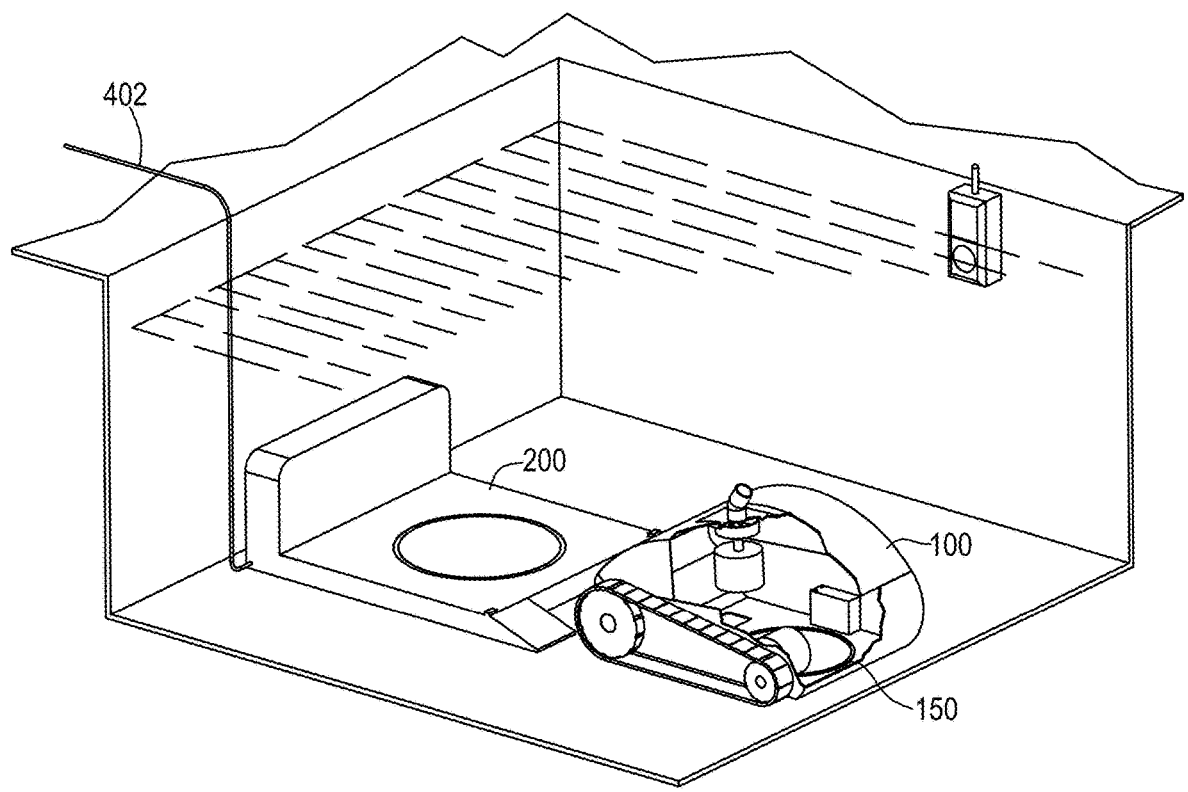
FIG. 3A illustrates a portion of a pool, a pool cleaning robot and an underwater station according to an embodiment of the invention.
Figure 3B:
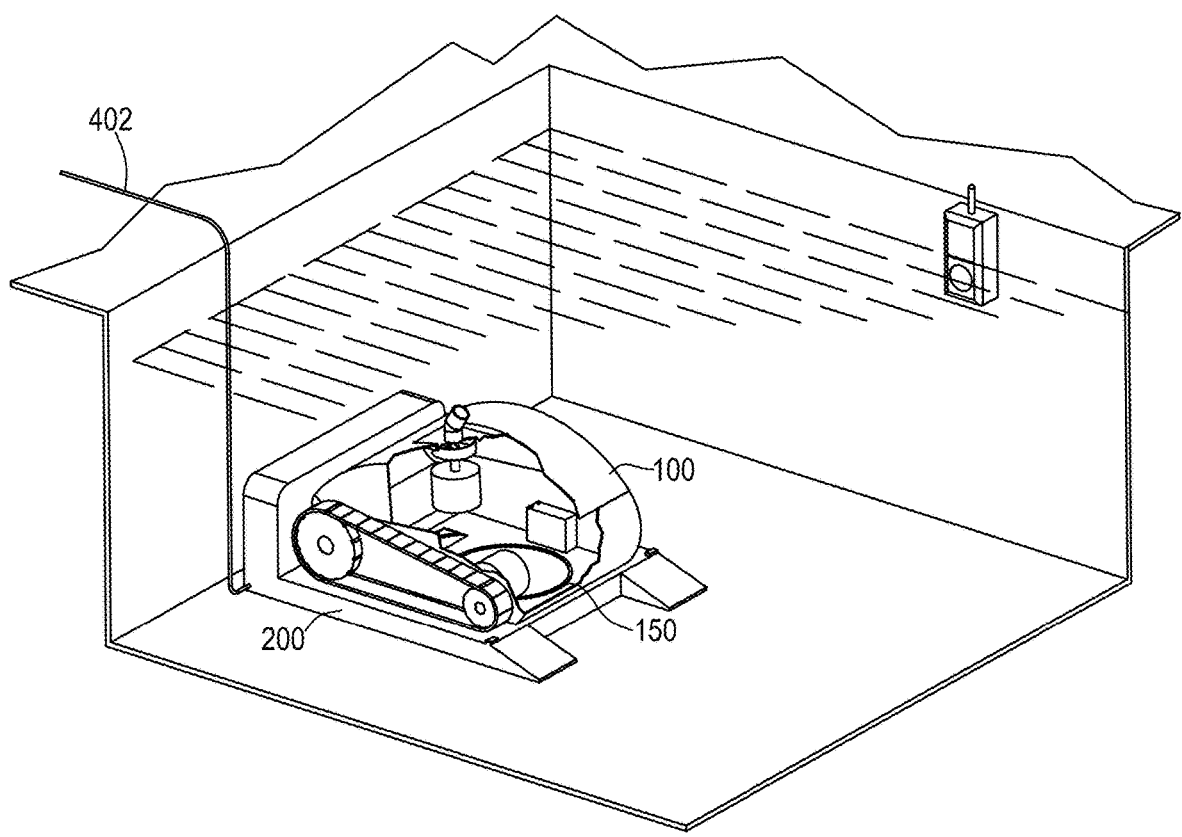
FIG. 3B illustrates a portion of a pool and pool cleaning robot that is wirelessly charged by an underwater station while being positioned on a platform of the underwater station according to an embodiment of the invention.

FIGS. 1 and 3A illustrate a pool cleaning robot 100 that approaches an underwater station 200 according to an embodiment of the invention. FIG. 3B illustrates a pool cleaning robot 100 that is mounted on an underwater station 200 according to an embodiment of the invention.

The underwater station of FIG. 1 is illustrated as including an erect portion 230, a platform 230 on which the pool cleaning robot can mount, a first contactless charging element 210, and radiation sources 241 and 242. Radiation sources 241 and 242 may be spaced apart from each other and are arranged to emit radiation (such as ultrasonic radiation) that can be detected by sensor 110 of pool cleaning robot 100 and allow the pool cleaning robot 100 to navigate towards the underwater station 200. The pool cleaning robot 100 may compare between the radiation received from the different radiation sources (241 and 242) and direct itself toward the underwater station 200. The radiation sources 241 and 242 may emit radiation of different frequencies, in different points of time and the like.

The platform 230 is illustrated as including flat surface 221 and rails 222 that ease the mounting of the pool cleaning robot on the flat surface 221. A first contactless charging element 210 may be connected to the platform 220, embedded in the platform 220 or otherwise included in the underwater station 200 and may be used to charge the pool cleaning robot 100 that in turn has a second contactless charging element (denoted 150 in FIGS. 3A and 3B) to facilitate the contactless charging of the pool cleaning robot 100. FIGS. 3A and 3B also illustrate a cable 402 that feeds the underwater station with electrical power. This electrical power can be supplied to the first contactless charging element 210.

FIG. 1 also illustrates a holding element such as ring 9 that can be contacted when the pool cleaning robot 100 is taken out of the pool.

Figure 4A:
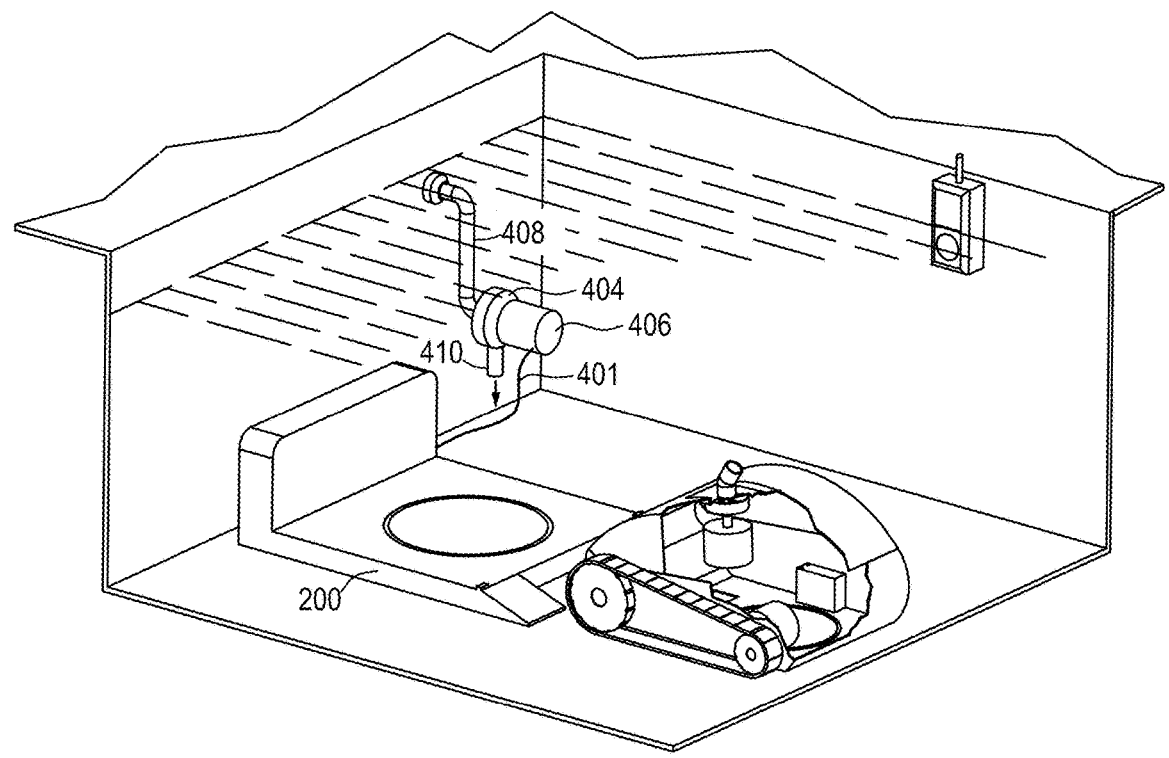
FIG. 4A illustrates a portion of a pool, a pool cleaning robot, an underwater station, a turbine, an electrical generator that feeds the underwater station and a tube of a pool fluid circulation system according to an embodiment of the invention.
Figure 4B:
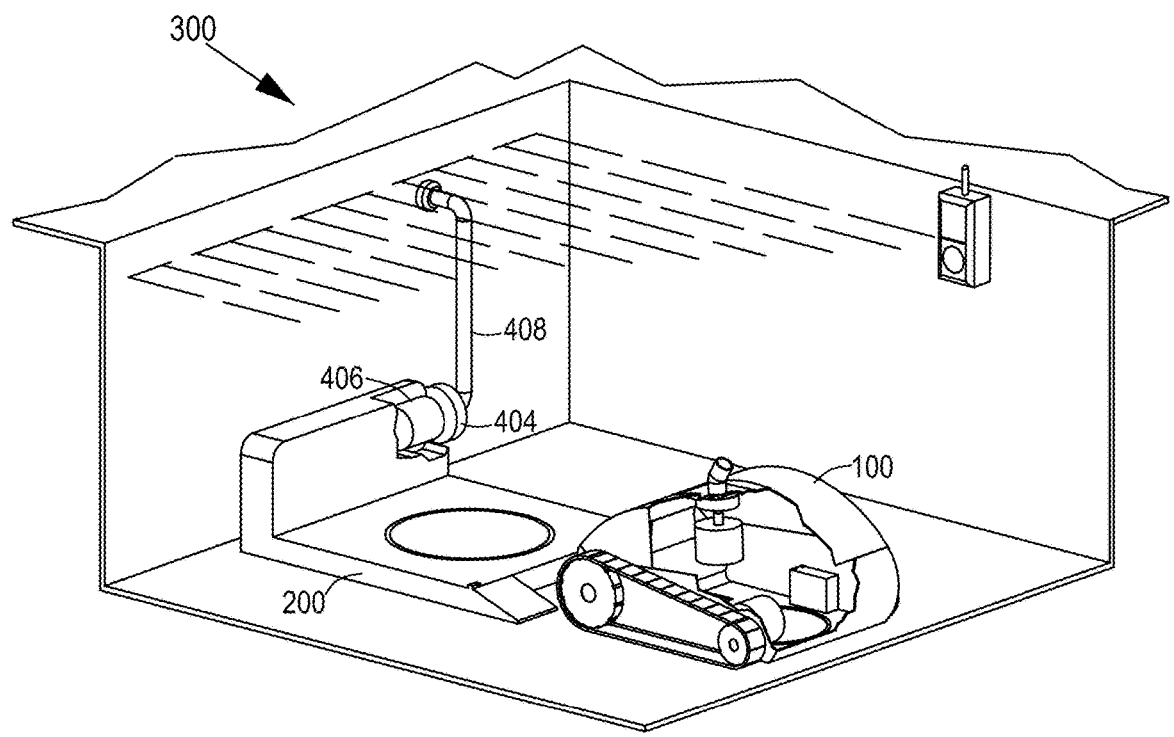
FIG. 4B illustrates a portion of a pool, a pool cleaning robot, an underwater station, a turbine, an electrical generator that form a part of the underwater station and a tube of a pool fluid circulation system according to an embodiment of the invention.

Charging a Pool Cleaning Robot Using a Flow of Fluid that Induced by a Pool Fluid Circulation System A pool cleaning robot may be charged using a flow of fluid that is induced by a pool fluid circulation system. A turbine that is rotated by the flow of fluid can be included in the pool cleaning robot (as shown in FIGS. 2A, 2B, 2C and 4C), can be included in an underwater station (as shown in FIG. 4B) or can be coupled to the underwater pool cleaning robot (as shown in FIG. 4A).

Figure 2A:
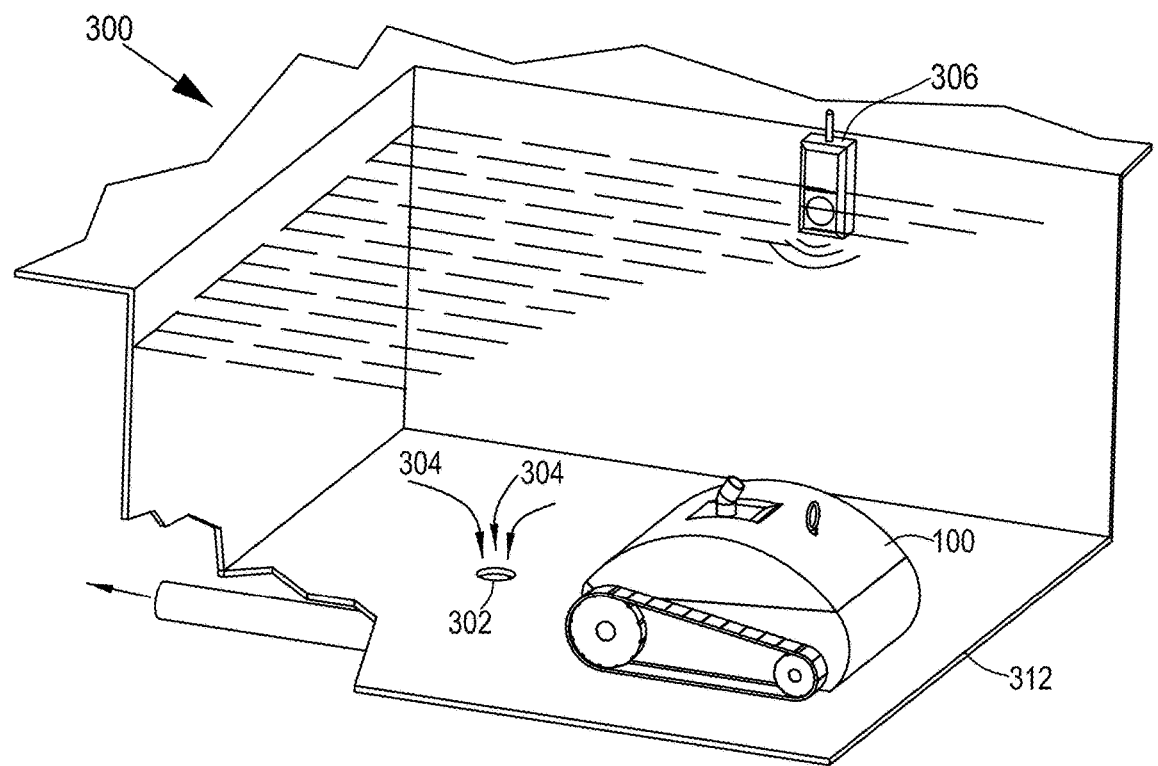
FIG. 2A illustrates a portion of a pool, a pool cleaning robot and a drain of the pool according to an embodiment of the invention.
Figure 2B:
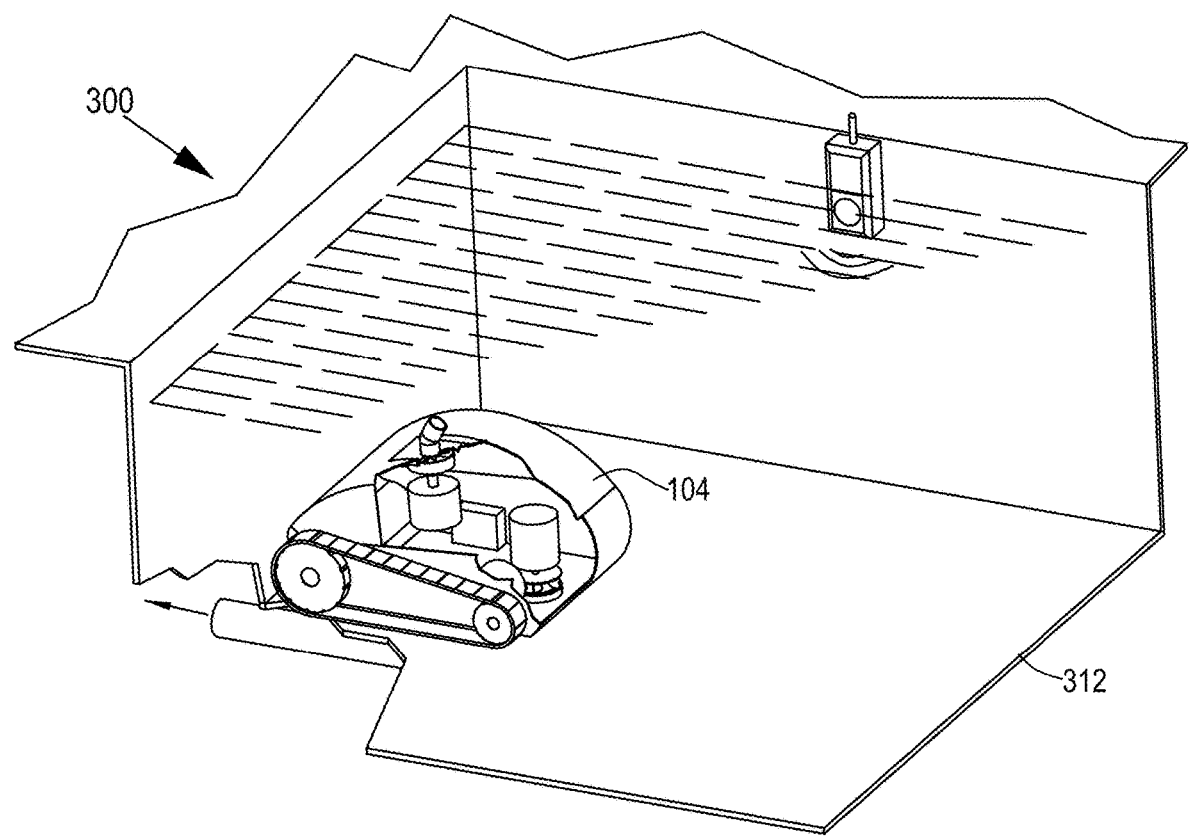
FIG. 2B illustrates a portion of a pool and a pool cleaning robot that is positioned on top of a drain of the pool according to an embodiment of the invention.
Figure 2C:
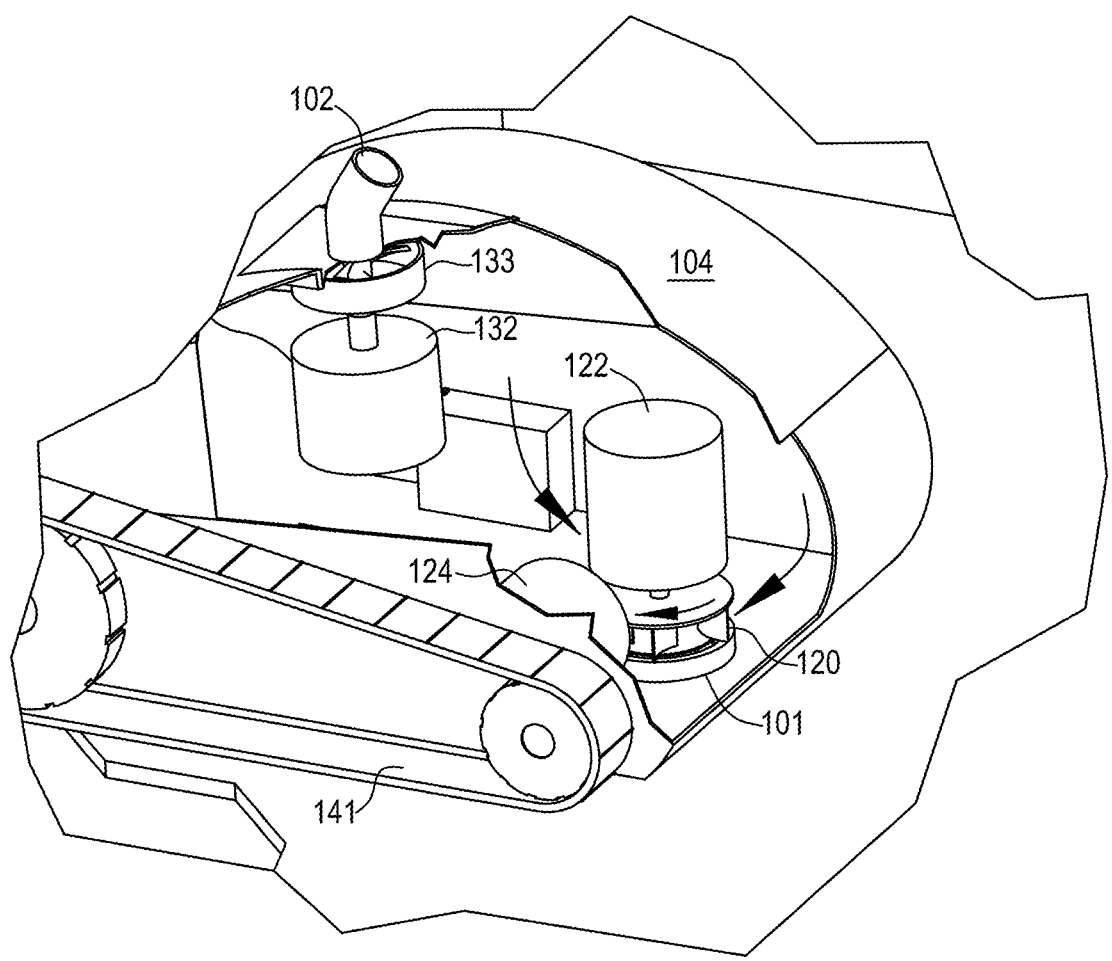
FIG. 2C illustrates a portion of a pool cleaning robot that is positioned on top of a drain of the pool according to an embodiment of the invention.

FIG. 2C illustrates a pool cleaning robot 100 while FIGS. 2A and 2B illustrate the pool cleaning robot 100 as well as a portion of a pool 300 and a drain 302 of the pool according to an embodiment of the invention. In FIG. 2A the pool cleaning robot 100 is near the drain 302 while in FIG. 2B the pool cleaning robot is on top of the drain (not shown). FIG. 2A also illustrates a communication module 306 for communication with the pool cleaning robot 100.

Referring to FIG. 2C—pool cleaning robot 100 includes turbine 120, housing 104, first fluid opening 101 and second fluid opening 102 formed in the housing 104, electrical generator 122, pump motor 132, impeller 133, rechargeable power source such as battery 135, drive motor 124 and first track 141. Non-limiting examples of additional and/or alternative components and modules of the pool cleaning robot 100 are illustrated in FIGS. 18A-18H.

The turbine 120 is positioned above a first fluid opening 101 formed at the bottom of the pool cleaning robot 100 and below second fluid opening 102.

The turbine 120 is at least partially disposed within a fluid path formed between the first fluid opening 101 so as to extract energy from flow of fluid through the fluid path.

Electrical generator 122 is arranged to provide electrical power thereto and adapted to be driven by the turbine 120.

The rechargeable power source 135 is arranged to be charged by the electrical generator 122 and to supply electrical power during at least one period of time during which the turbine 120 does not extract energy from the flow of fluid.

When positioned in proximity of the drain 302, fluid is sucked from second fluid outlet 102, through the fluid path and exits the pool cleaning robot via the first fluid opening 101 thereby rotating the turbine 120.

Figure 20:
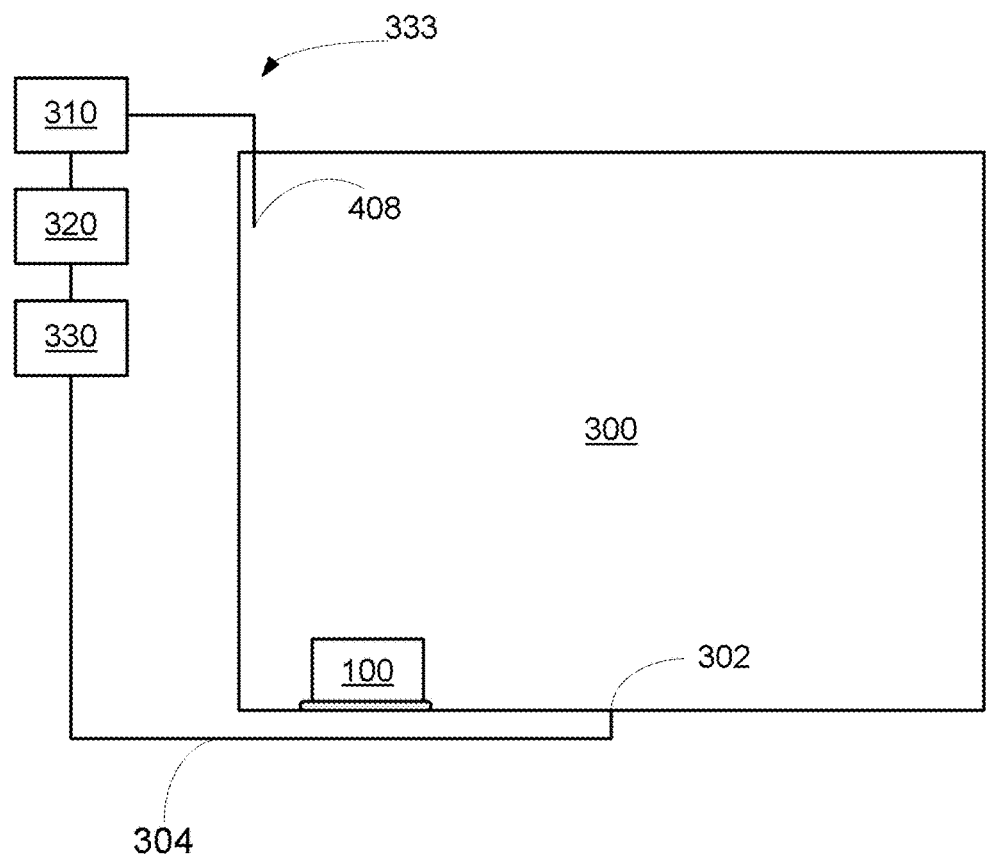
FIG. 20 illustrates a pool, a poll pool cleaning robot and a pool fluid circulation system according to an embodiment of the invention.

It is noted that charging the pool cleaning robot 100 by the drain 302 is an example of charging the pool cleaning robot by a flow of fluid that is induced by a pool fluid circulation system (denoted 333 in FIG. 20A).

Yet for another example—pool cleaning robot may be located in proximity (or in contact with) an output of a tube (denoted 408 in FIG. 4C) of the pool fluid circulation system.

It is expected that the pool cleaning robot 100 needs to be relatively proximate (few centimeters till few tenths of centimeters) from an inlet or outlet of the pool fluid circulation system in order that a sufficient amount of flow of fluid is induced to flow through the fluid path and thereby rotating turbine 120.

Accordingly—the charging may occur when the pool cleaning robot 100 is positioned in a certain location in which a flow level of fluid that is circulated by a pool fluid circulation system is higher than a flow level of the fluid within a majority of the pool or even be the highest flow level in the pool. When positioned at the certain location the fluid that is circulated by the pool fluid circulation system passes through the fluid path formed in the pool cleaning robot.

FIG. 4A illustrates a portion of a pool 300, a pool cleaning robot 100, an underwater station 200, a turbine 404, an electrical generator 406 that feeds the underwater station 200 with electrical power via cable 401 and a tube 408 of a pool fluid circulation system according to an embodiment of the invention. Turbine 404 and electrical generator 406 are submerged and do not belong to the underwater station 200 or to the pool cleaning robot 100. Tube 408 can direct a jet of fluid towards turbine 404 or may such fluid from the pool. Turbine has an outlet 410 for allowing fluid that is jetted by the tube 408 to enter the pool and/or to allow fluid sucked through tube 408 to enter turbine 404.

FIG. 4B illustrates a portion of a pool 300, a pool cleaning robot 100, an underwater station 200 as well as a turbine 404 and an electrical generator 406 that form a part of the underwater station 200 that feeds the underwater station according to an embodiment of the invention. Turbine 404 is rotated by a flow of fluid induced by tube 408 of the pool fluid circulation system.

Figure 4C:
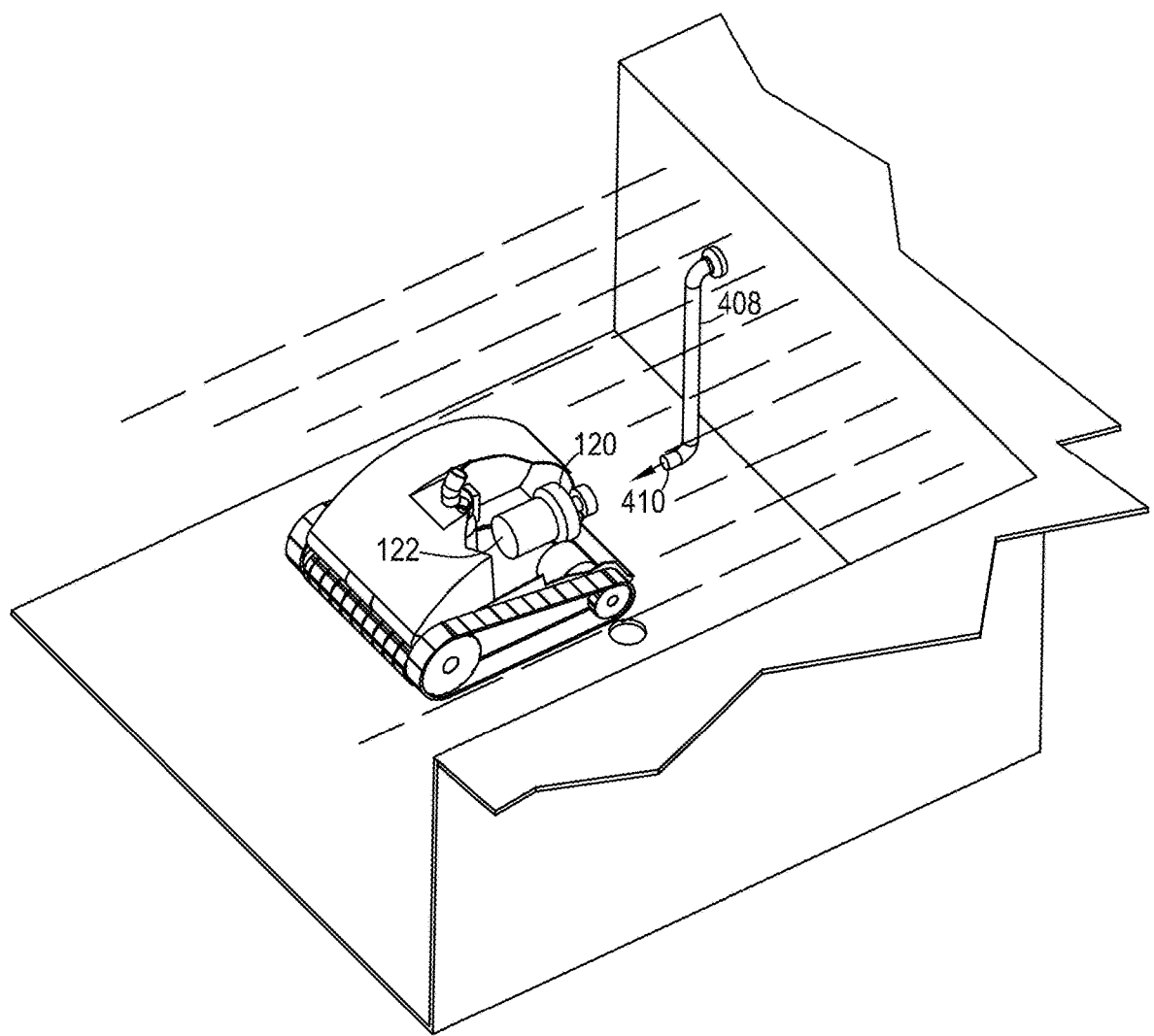
FIG. 4C illustrates a portion of a pool, a pool cleaning robot that includes a turbine and an electrical generator and a tube of a pool fluid circulation system according to an embodiment of the invention.

FIG. 4C illustrates a portion of a pool 300, tube 408 and a pool cleaning robot 100 that includes turbine 404 and electrical generator 406 according to an embodiment of the invention. The turbine 404 is rotated by a flow of fluid induced by tube 408 of the pool fluid circulation system. This may require the pool cleaning robot to direct turbine 404 (facing one of the sides of the pool cleaning robot—but not its bottom) to be positioned near the opening of tube 408.

Underwater Filter Replacement

Additionally or alternatively, filters of the pool cleaning robot can be inserted to the pool cleaning robot underwater, ejected from the pool cleaning robot underwater, replaced underwater and/or processed underwater. The insertion and/or the ejection and/or the replacement of the filters can be executed by the robot, by an underwater station of by a combination of both.

Figure 5A:
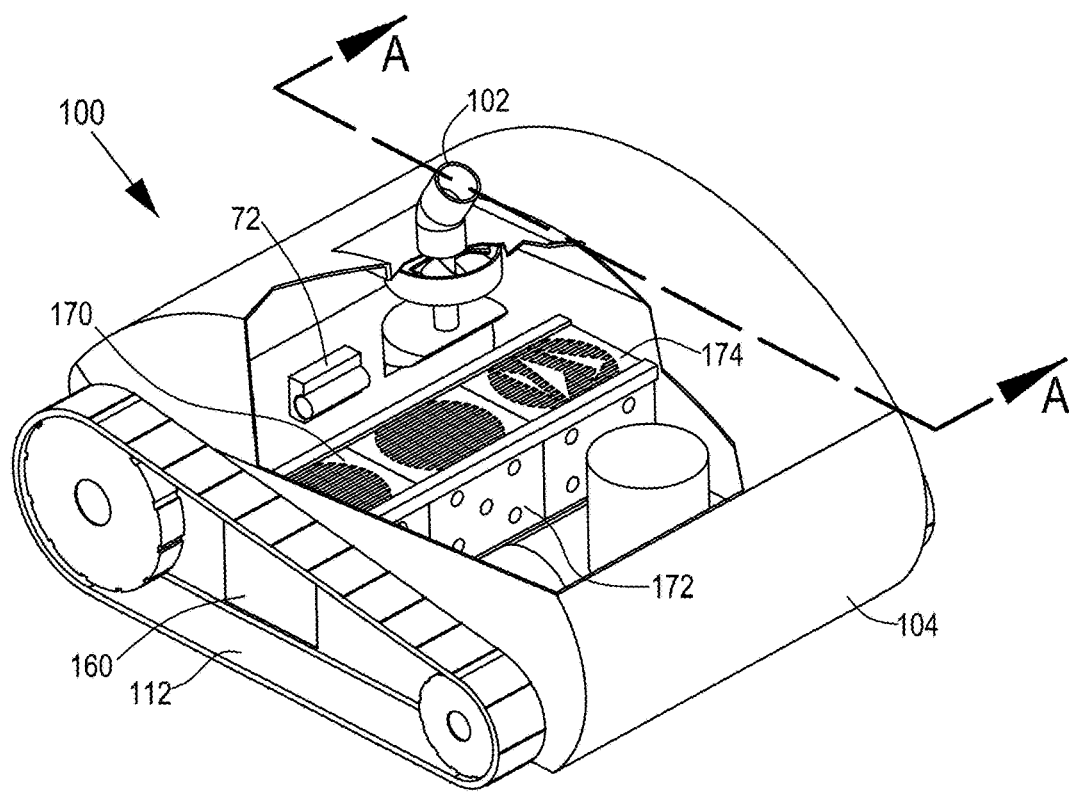
FIG. 5A illustrates a pool cleaning robot that includes multiple filters according to an embodiment of the invention.
Figure 5B:
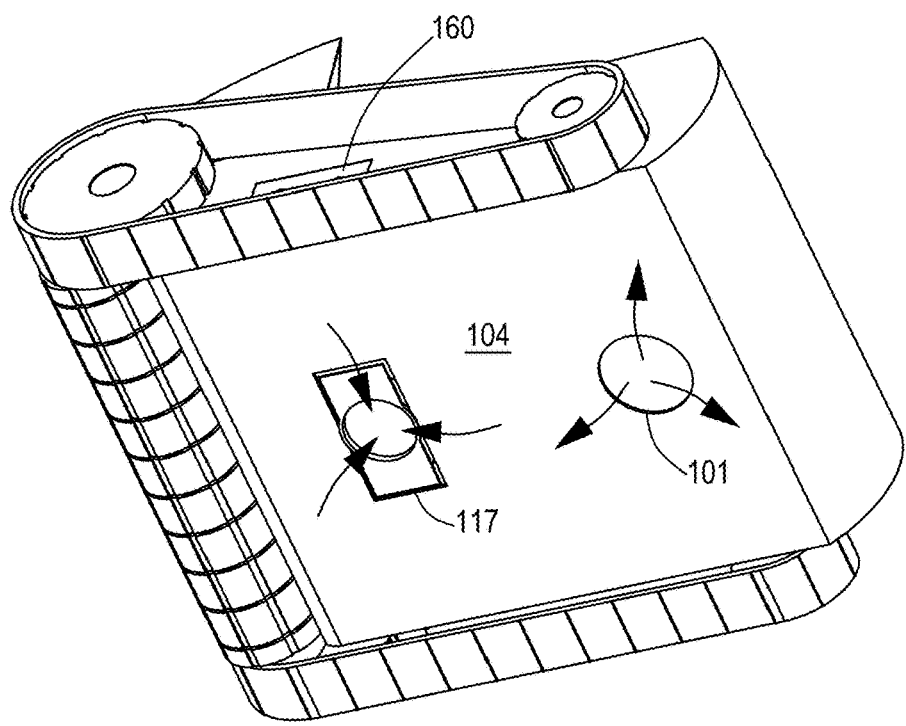
FIG. 5B illustrates a bottom of a housing of a pool cleaning robot that includes multiple filters according to an embodiment of the invention.
Figure 5C:
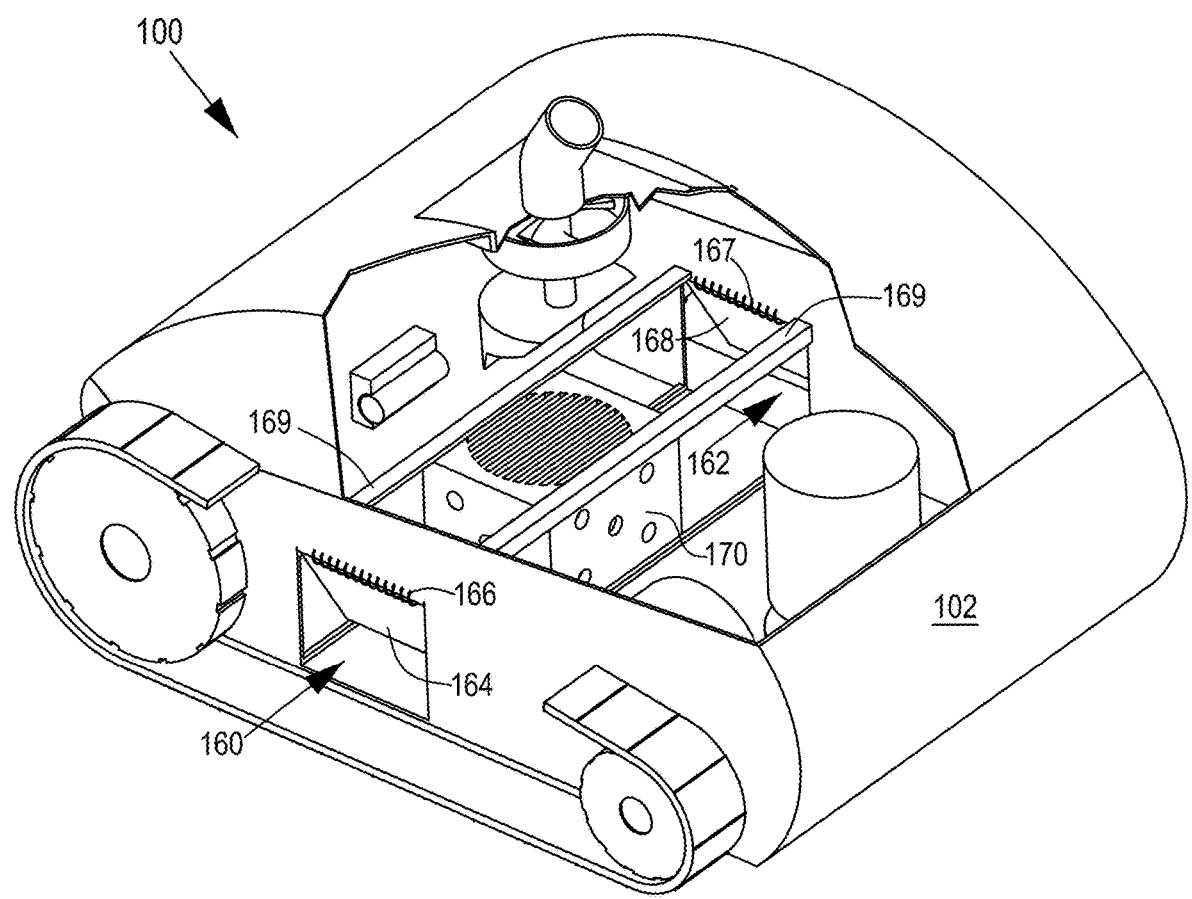
FIG. 5C illustrates a pool cleaning robot that includes a filter according to an embodiment of the invention.

FIG. 5A illustrates a pool cleaning robot 100 that includes multiple filters 170, 172 and 174 according to an embodiment of the invention. FIG. 5B illustrates a bottom of a housing 104 of a pool cleaning robot 100 that includes multiple filters according to an embodiment of the invention. FIG. 5C illustrates a pool cleaning robot 100 that includes a single filter 170 according to an embodiment of the invention.

Filter 172 may be used to filter the fluid that passes through the pool cleaning robot 100—as may be regarded as being in a filtering position. The fluid may enter through fluid opening 117 (see FIG. 5B).

Filters 172 and 174 may be regarded as being in a non-filtering position.

Alternatively—more than one of the filters 170, 172 and 174 can be used for concurrently filtering fluid that passes through the pool cleaning robot 100.

Alternatively—filter 170 or filter 174 can be used for filtering while filter 172 is not be used for filtering—when positioned at the center of the pool cleaning robot 100

Filters 170, 172 and 174 may be inserted through a first filter opening 160 formed in the housing of the pool cleaning robot 100.

Filters 170, 172 and 174 may be ejected (outputted) from the pool cleaning robot through the first filter opening 160 or (As illustrated in FIGS. 5A and 5C)—through a second filter opening (denoted 162 formed in the housing of the pool cleaning robot 100).

Between insertion and ejection the filters of FIGS. 5A and 5C follow a linear path (delimited by rails 169) that is normal to the longitudinal axis of the pool cleaning robot. It is noted that other paths (non-linear, other linear paths) can be provided.

Filter openings may be positioned in various locations of the housing—including the bottom of the housing, the upper portion of the housing or any side portions (sidewalls) of the housing. FIGS. 5A-5C merely illustrates a non-limiting of the locations of such filter openings.

FIG. 5A also illustrates a sanitizing unit 72 that is arranged to irradiate a filter with ultraviolet radiation or perform any other sanitizing process.

Referring to FIG. 5C—first filter opening 160 is equipped with a first door 164 and a spring mechanism 166 that allows the first door 164 to open when a filter is inserted to the pool cleaning robot 100 and to be closed (thereby closing the first filter opening 160) after the filter is inserted.

Second filter opening 162 is equipped with a second door 168 and a spring mechanism 169 that allows the second door 168 to open when a filter is extracted/ejected/outputted from the pool cleaning robot 100 and to be closed (thereby closing the second filter opening 162) after the filter is extracted/ejected/outputted.

It is noted that a filter opening can be closed by the filter (or by the filter housing)—as illustrated in FIG. 5A.

Figure 6A:
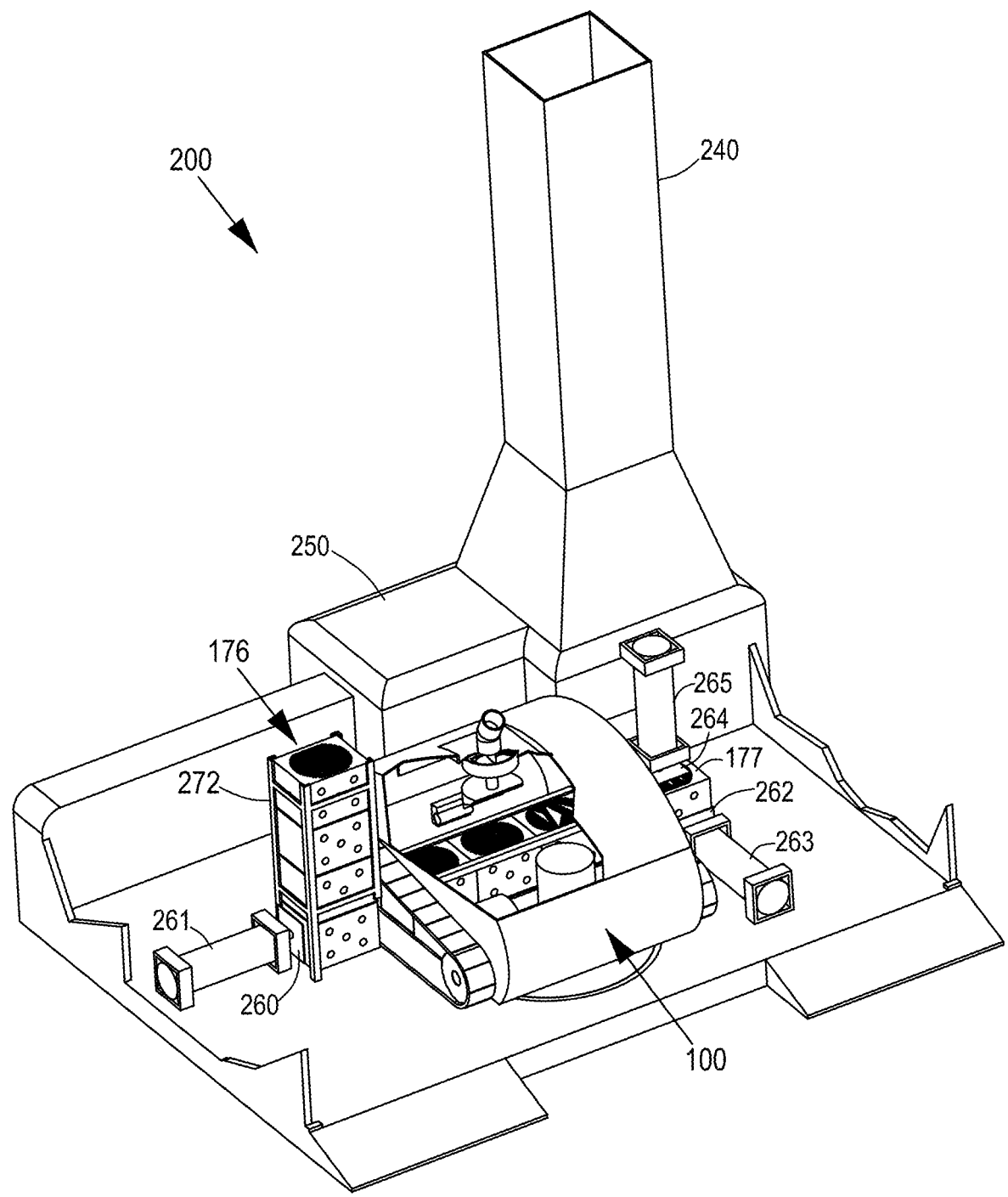
FIG. 6A illustrates a pool cleaning robot, an underwater station and multiple filters according to an embodiment of the invention.
Figure 6B:
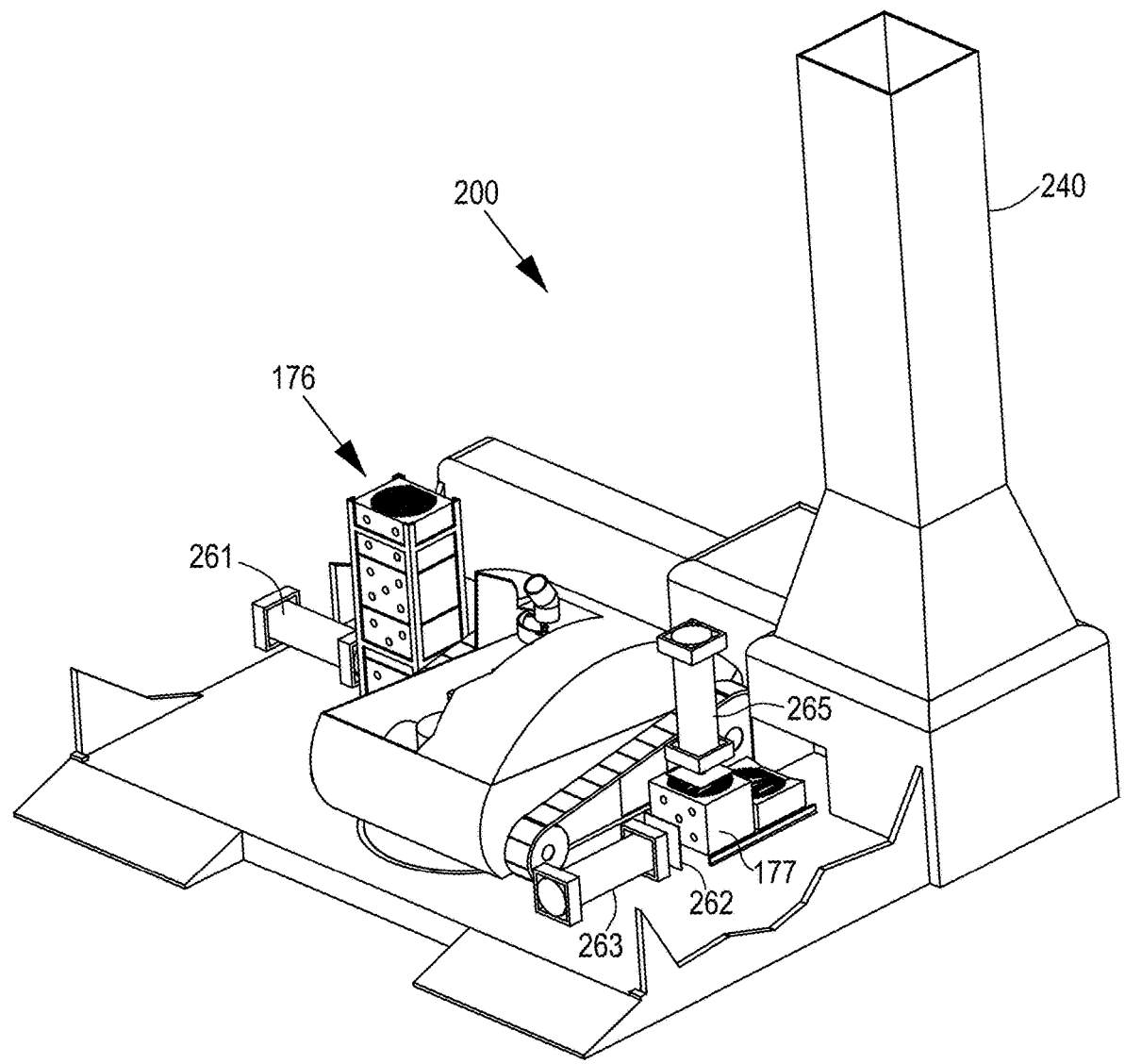
FIG. 6B illustrates a pool cleaning robot, an underwater station and multiple filters according to an embodiment of the invention.

FIGS. 6A and 6B illustrates a pool cleaning robot 100, an underwater station 200 and multiple filters 176 and 177 according to an embodiment of the invention.

The pool cleaning robot 100 is mounted on the underwater station 200. Filters 176 are stored in a first filter storage module 272 and then fed to the pool cleaning robot 100 by a first filter manipulator that is represented by arm 261. Filters are ejected from the pool cleaning robot 100 by the first filter manipulator (if the same movement used for inserting filters can also eject filters) or by a second filter manipulator that is represented by arm 263 that pushes used filters into underwater station housing 250.

FIGS. 6A and 6B also illustrate a compressor (represented by arm 265) that compresses a used filter before the used filter enters underwater station housing 250.

The underwater station 200 is further illustrated as including underwater station housing 250 and filter ejection module 240 from which used filters can be ejected or otherwise taken outside the pool.

The underwater station 200 is illustrated as including a duct 240 through which used filters can float, ejected or taken outside the pool.

The underwater station 200 may include processing elements located within the housing 250 (or outside the housing) for sanitizing, shredding, compressing, and/or attaching floating elements to used filters.

Figure 7A:
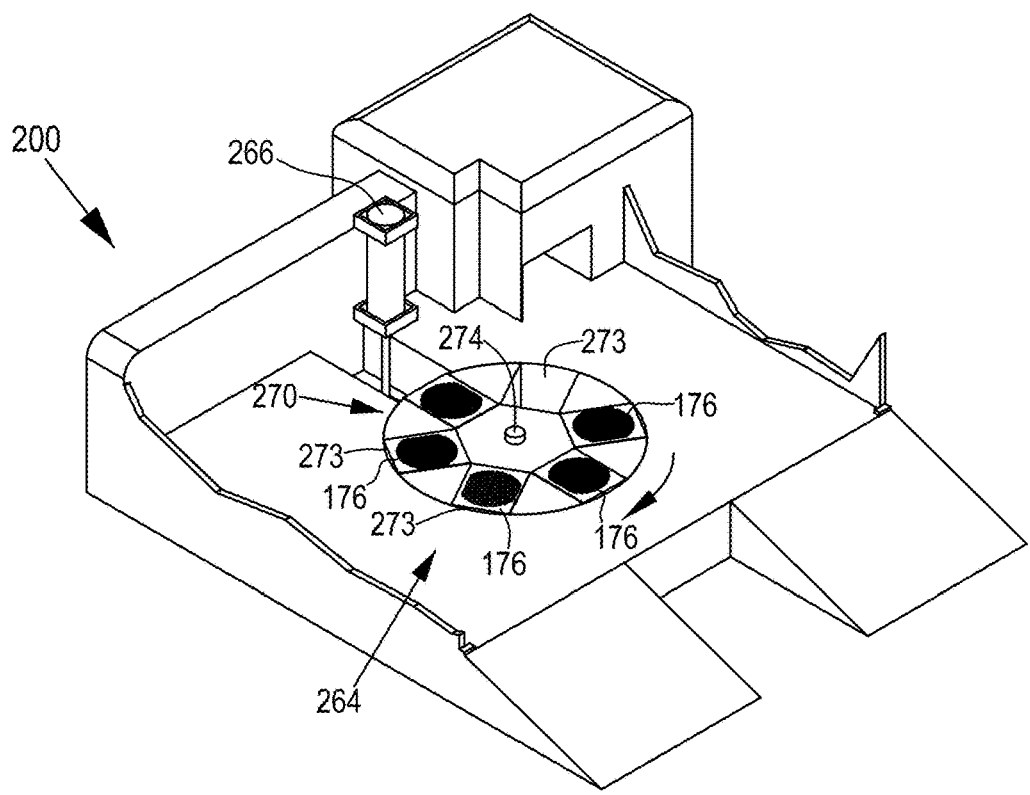
FIG. 7A illustrates an underwater station that comprises a filter manipulator according to an embodiment of the invention.
Figure 7B:
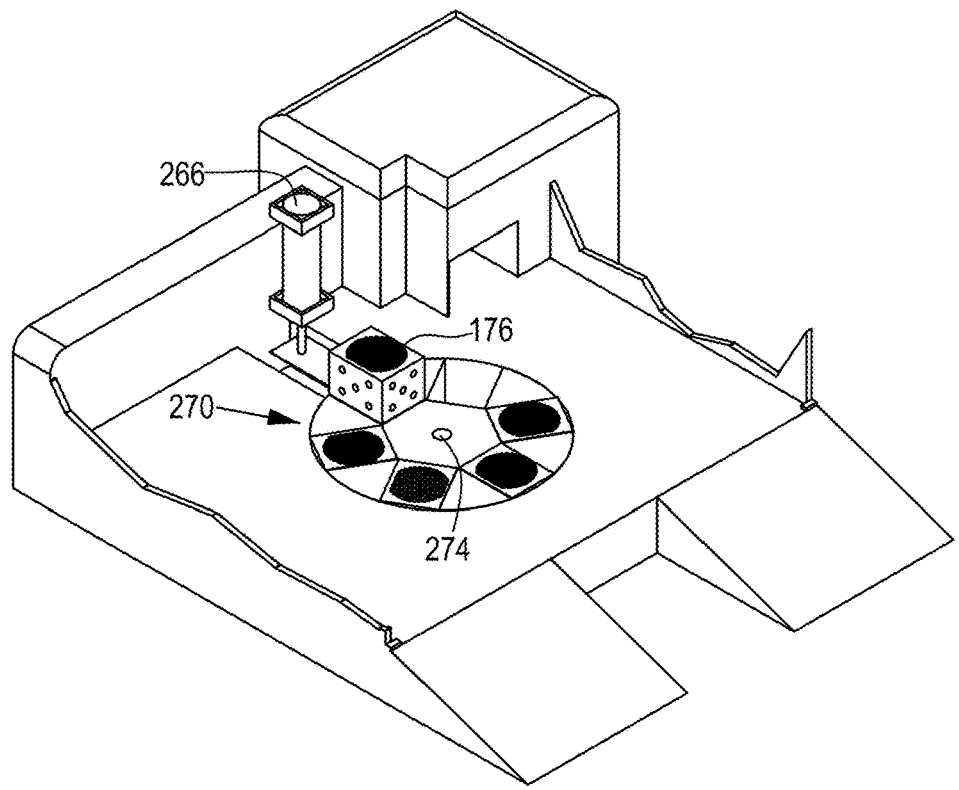
FIG. 7B illustrates an underwater station that comprises a filter manipulator that elevates a filter to be inserted into a pool cleaning robot according to an embodiment of the invention.
Figure 7C:
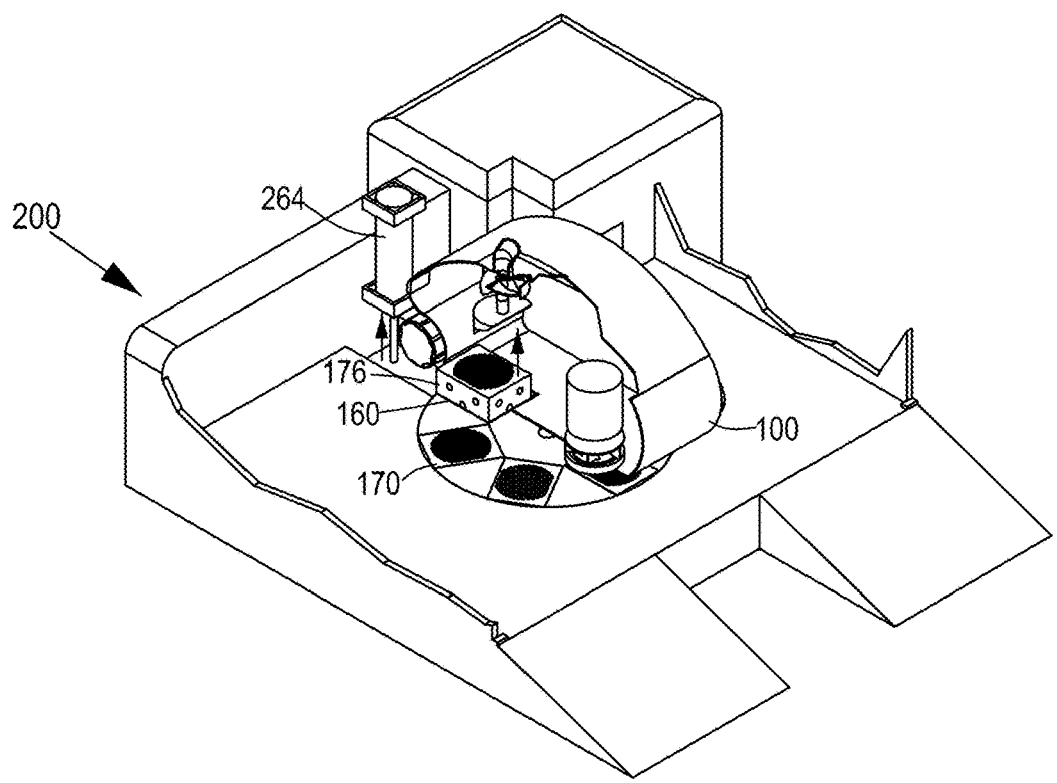
FIG. 7C illustrates an underwater station that comprises a filter manipulator and pool cleaning robot that is positioned on a platform of the underwater station and is fed by a filter according to an embodiment of the invention.
Figure 7D:
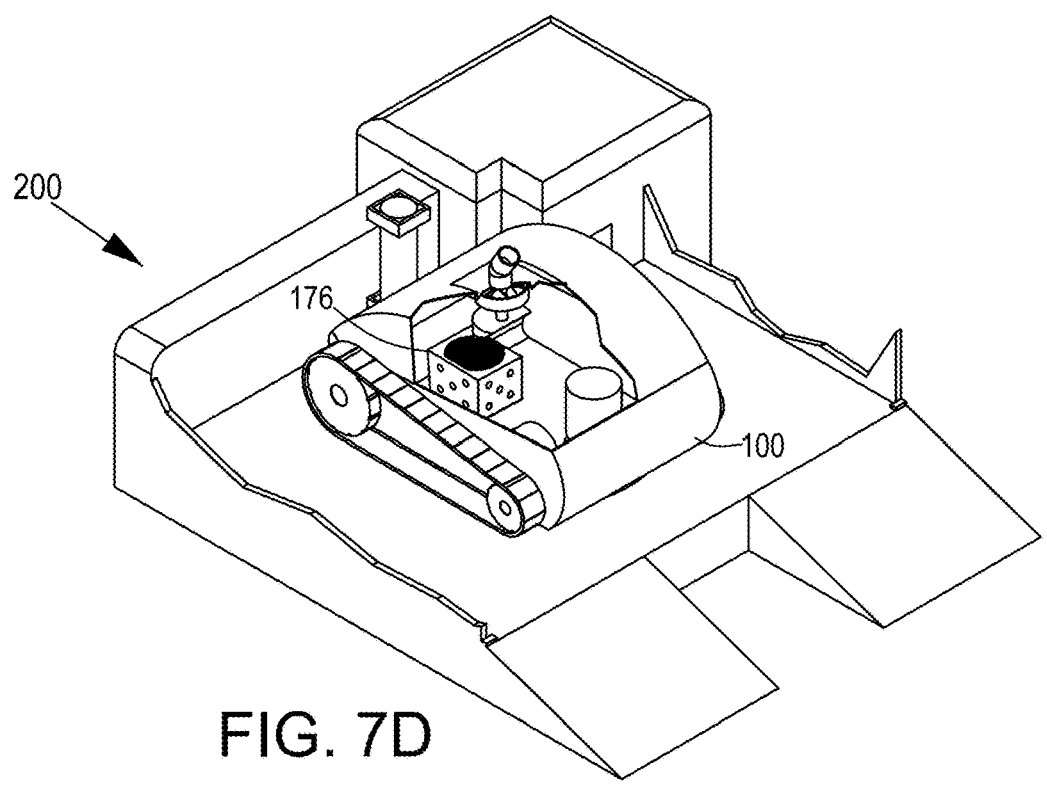
FIG. 7D illustrates an underwater station that comprises a filter manipulator and pool cleaning robot that is positioned on a platform of the underwater station after being fed by a filter according to an embodiment of the invention.

FIG. 7A-7D illustrate an underwater station 200 during various stages of a loading process of a filter into a pool cleaning robot 100 according to an embodiment of the invention. FIGS. 7C and 7D also illustrate the pool cleaning robot 100 that is being loaded with a filter.

The underwater station 200 includes a filter manipulator that includes a arm 266 for elevating a filter from a filter storage module 270 that may have a radially symmetrical shape (annular, cylindrical and the like) that has multiple compartments 273 for storing multiple filters 176. The filter storage module 270 is rotated about its center by a movement module that has an axel denoted 274 for rotating the filter storage module 270 about its axis—thereby selecting a selected filter to be inserted to the pool cleaning robot 100 via an opening formed at the bottom of the housing of the pool cleaning robot. The selected filter is positioned in proximity to arm 266 in order to allow arm 266 to elevate the filter into the pool cleaning robot 100. FIG. 7A illustrates a positioning of a selected filter near arm 266. FIGS. 7B-7C illustrates phases in the lifting process and FIG. 7D shows the end of the lifting process.

An opposite process may be used to extract a used filter from the pool cleaning robot 100—the arm 266 contacts the filter and lowers it to an empty compartment of the filter storage module 270.

Figure 8:
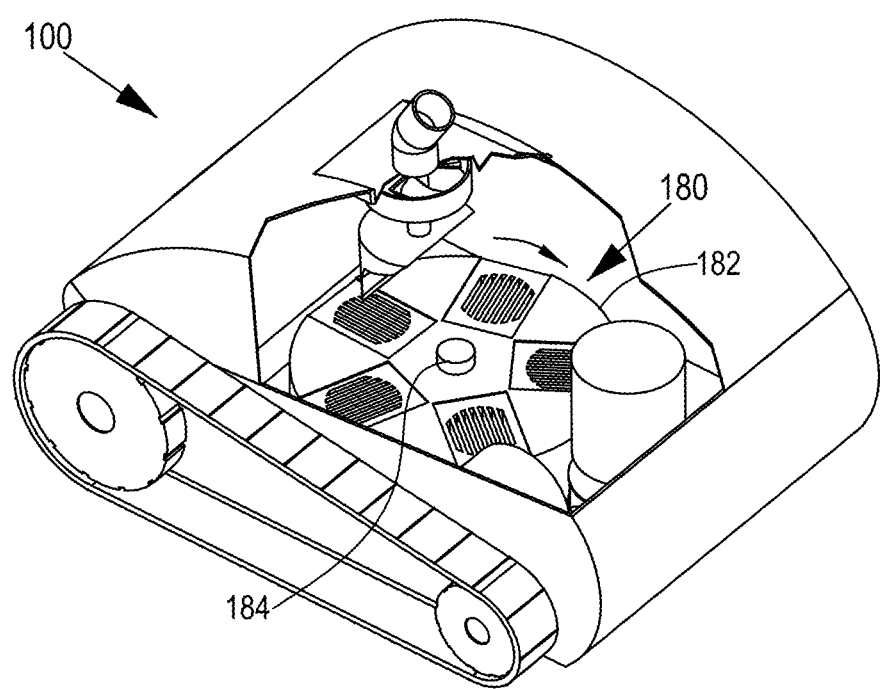
FIG. 8 illustrates a pool cleaning robot that comprises a filter according to an embodiment of the invention.

FIG. 8 illustrates a pool cleaning robot 100 that comprises a filter manipulator 180 and multiple filters according to an embodiment of the invention.

The filter manipulator 180 includes a filter storage module 182 that has multiple compartments for storing multiple filters. The filter storage module 182 may be have a radially symmetrical shape (annular, cylindrical and the like) and is rotated about its center by a movement module that has an axel denoted 184 for rotating the filter storage module 180 about its axis—thereby placing a selected filter in a filtering position.

The entire filter storage module 182 can be manually or automatically replaced. The latter can be executed by an underwater station or by the pool cleaning robot itself.

Filter Having a Rotatable Core

According to various embodiments of the invention there are provided filters that have filter cores that are rotatable. The rotation may introduce a centrifugal force that pushes compresses dirt towards the exterior of the filter and/or towards filtering elements of the filter and improves the filtering process.

Figure 9:
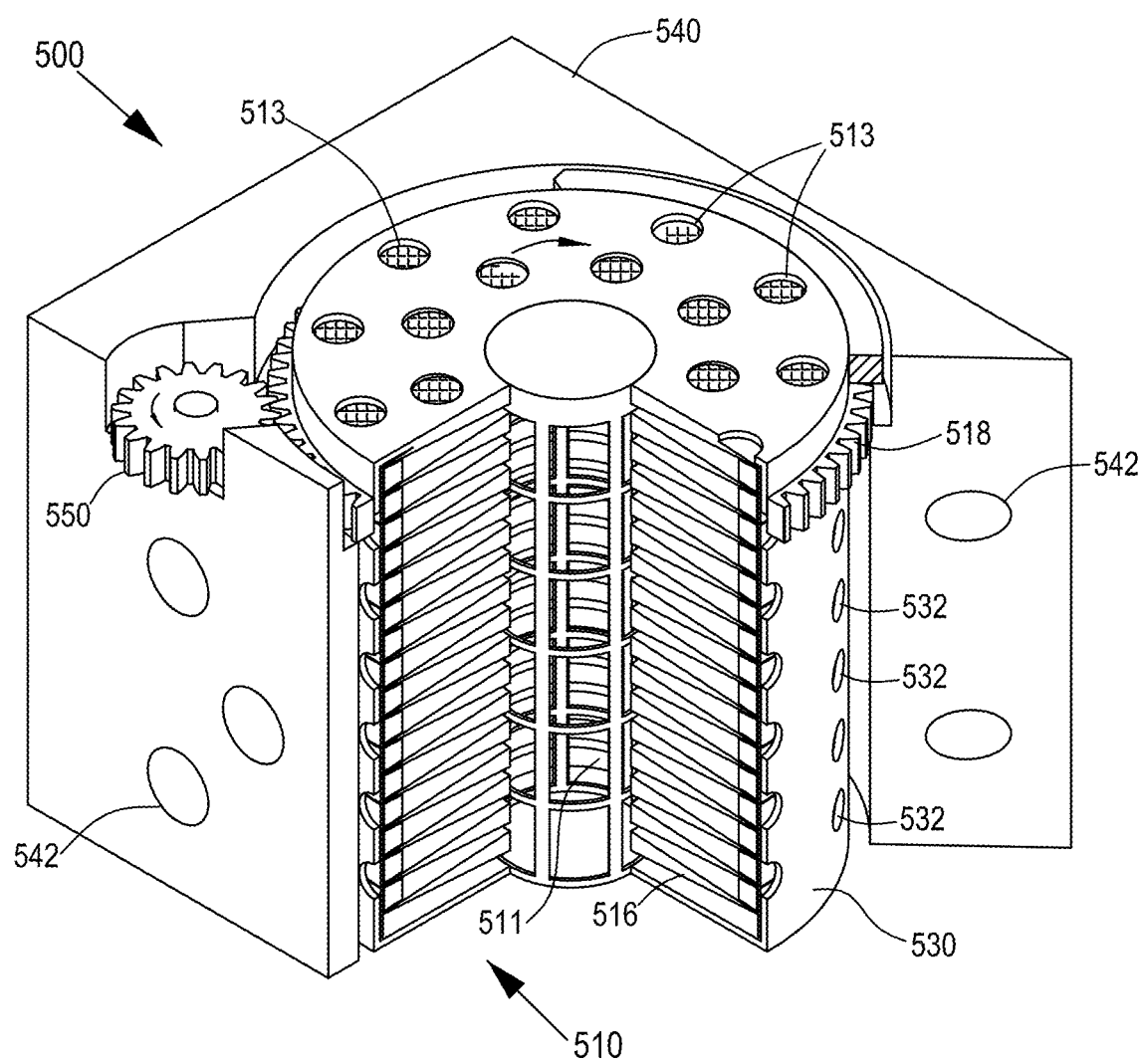
FIG. 9 illustrates a filter having a filter core with a zigzag shaped array of filtering elements, a perforated pole and a gear that assist in rotating a core of the filter according to an embodiment of the invention.

FIG. 9 illustrates a filter 500 that includes a filter core 510, a filter core enclosure 530 and filter housing 540.

It is noted that in various figures (for example FIGS. 9, 10, 12, 13A, 13B, 14, 15, 16A, 16B) there is illustrated a gap between the filter enclosure 530 and the filter housing 540. Such a gap may not exist or otherwise fluid can be prevented from passing through the gap unfiltered and enter various parts of the pool cleaning robot.

The filter core 510 is at least partially located within the filter housing 540 and includes one or more inlets 511, one or more outlets 513 and at least one filtering element (such as the zigzag array of filtering elements 516) that is positioned between the one or more inlets 511 and the an one or more outlets 513. The filter core enclosure 530 includes openings 532 that facilitate a flow of fluid to and from the filter core 510.

The filter core enclosure 530 includes a gear 518 that meshes with another gear 550. The other gear may be rotatably connected to the filter housing 540 and is rotated by a filter core rotator (denoted 552 in FIG. 11B).

The filter housing 540 includes filter housing openings 542 that facilitates a flow of fluid to and from the filter core enclosure 530.

FIG. 9 illustrates a cylindrical shaped filter core enclosure and a filter housing having a cylindrical interior and a rectangular shaped exterior. The filter core 510, the filter enclosure 530 and the filter housing 540 can be of different shapes.

FIG. 9 also illustrated a perforated pole 560 that is located at the center of the filter core 510. The perforated pole 560 can be regarded as belonging to filter 500 or as not belonging to the filter 500. The perforated pole 560 can be attached to the filter 500 in a detachable or non-detachable manner. For example an actuator and a spring may be provided for detaching or locking the filter.

Figure 10:
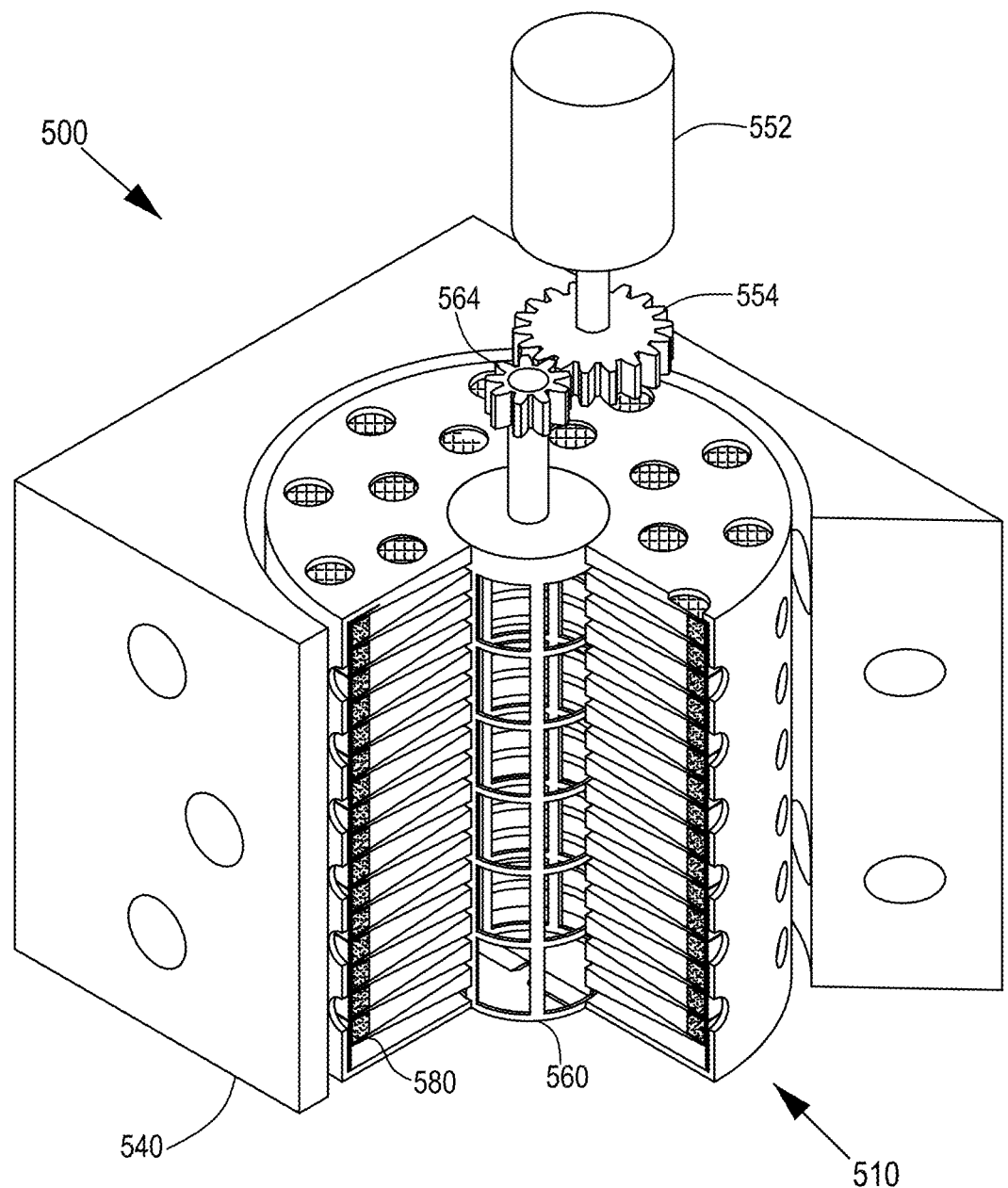
FIG. 10 illustrates a filter a filter core with zigzag shaped array of filtering elements, a gear and a perforated pole that assist in rotating the filter and a filter core rotator according to an embodiment of the invention.

FIG. 10 illustrates filter 500 as having (or being connected to) a perforated pole 560 that is connected to axel 562 that has a gear 564 at its top. Gear 564 is rotated by another gear 554 connected to filter core rotator 552. In FIG. 10 the filter housing 540 is not connected to gear 550 and the filter enclosure 530 does not include a gear.

Figure 11A:
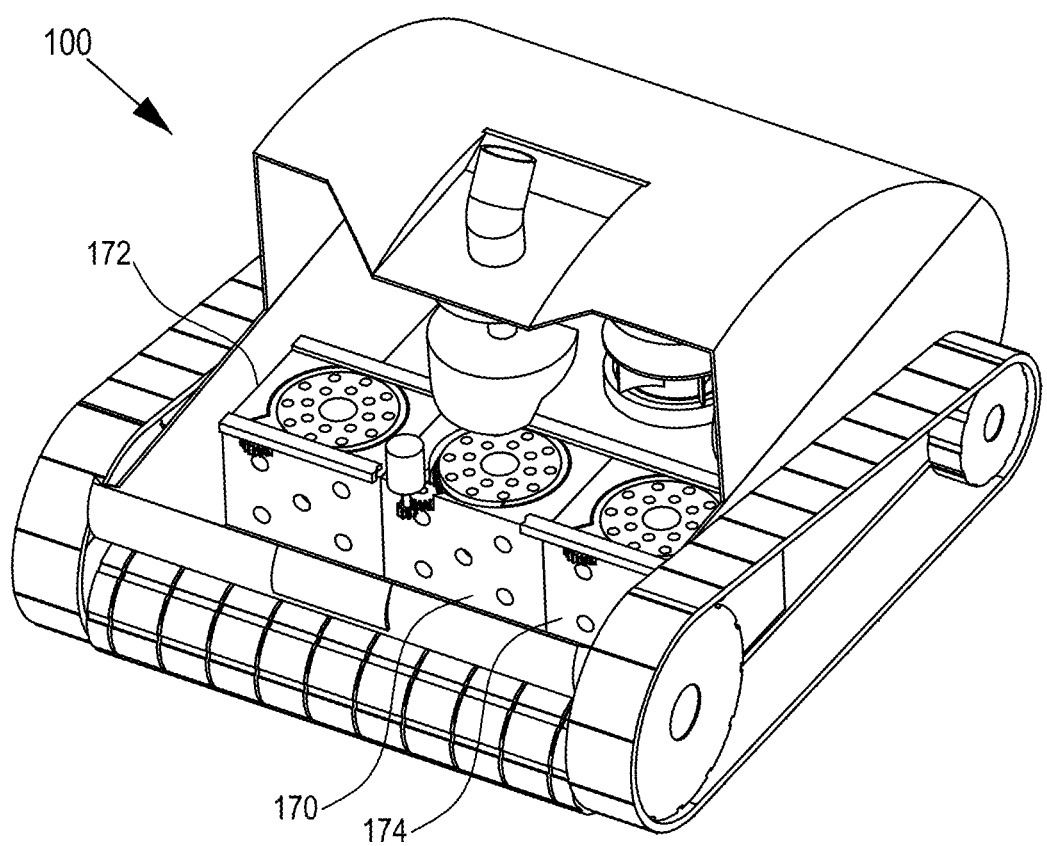
FIG. 11A illustrates a pool cleaning robot that includes multiple filters, a gear and a filter core rotator according to an embodiment of the invention.
Figure 11B:
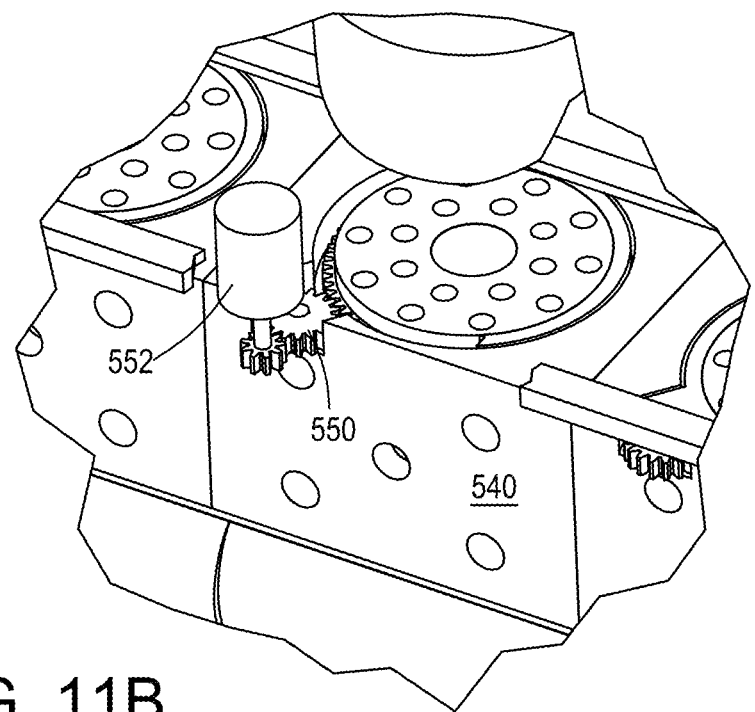
FIG. 11B illustrates multiple filters positioned within a pool cleaning robot, a gear and a filter core rotator according to an embodiment of the invention.

FIGS. 11A and 11B illustrate a pool cleaning robot 100 that includes multiple filters 170, 172 and 174, a gear 550 of filter 172 that is positioned in a filtering position and is rotated by filter core rotator 552 according to an embodiment of the invention.

Figure 12:
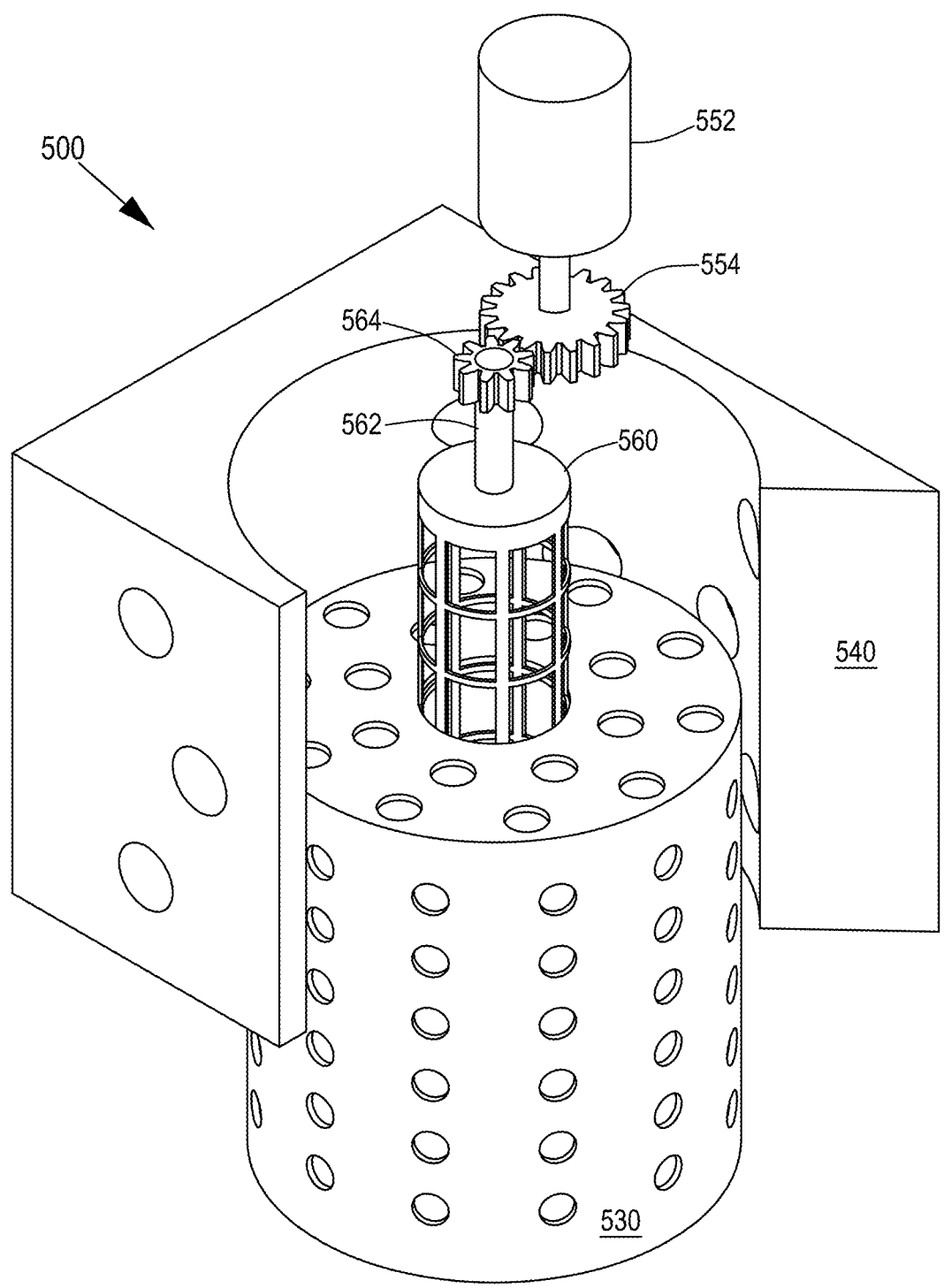
FIG. 12 illustrates a filter, a gear and a perforated pole, a filter core rotator while the filter core is being inserted to (or extracted from) the filter housing according to an embodiment of the invention.

FIG. 12 illustrates filter 500 as having (or being connected to) a perforated pole 560 that is connected to axel 562 that has a gear 564 at its top. Gear 564 is rotated by another gear 554 connected to filter core rotator 552. The filter core rotator 552 may be a pump motor, a drive motor or be mechanically coupled to one of these motors.

The filter core 510 can be inserted to (or extracted from) the filter housing 540. The filter housing 540 can be part of the filter and/or can be a part of the pool cleaning robot.

Figure 13A:
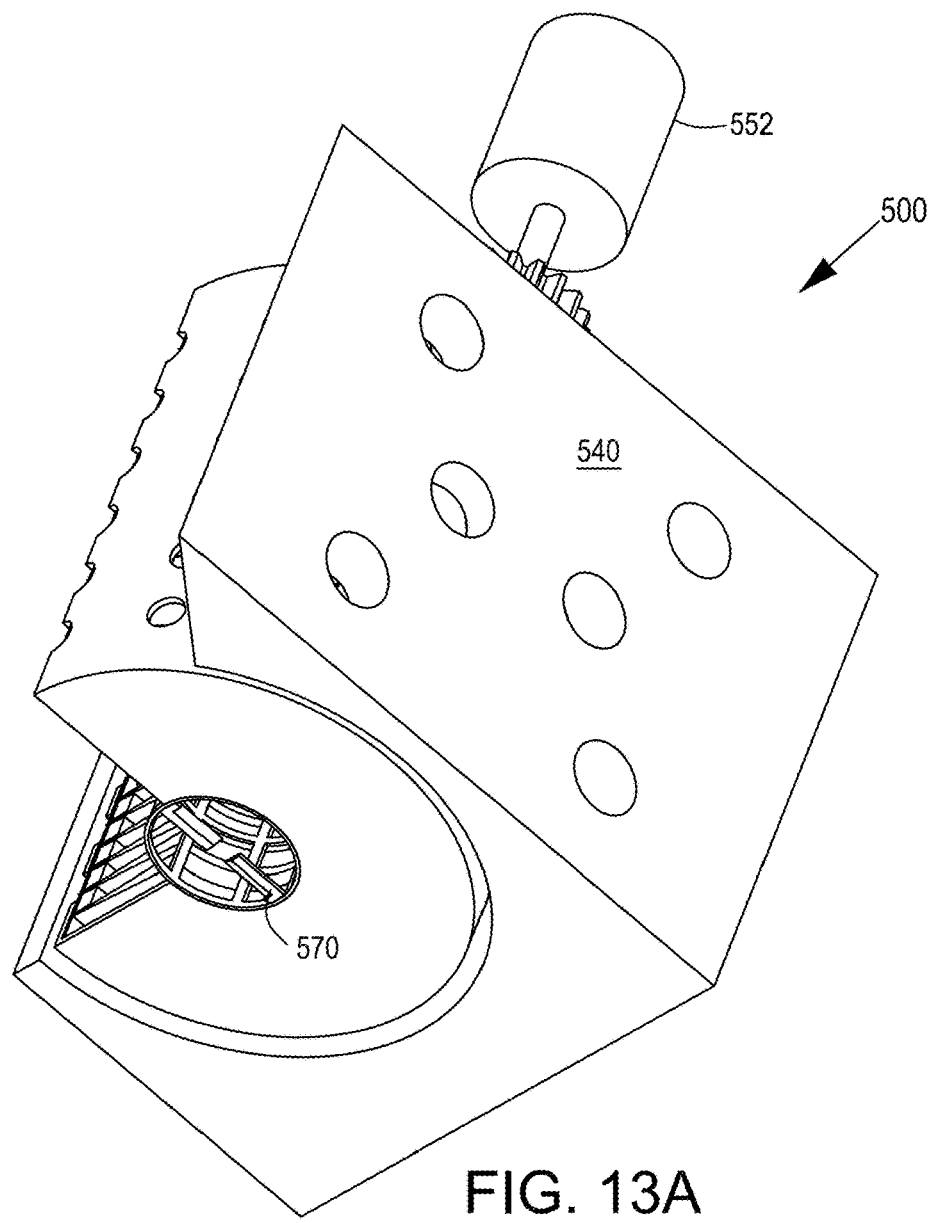
FIG. 13A illustrates a filter, a gear, a perforated pole, choppers, and a filter core rotator according to an embodiment of the invention.
Figure 13B:
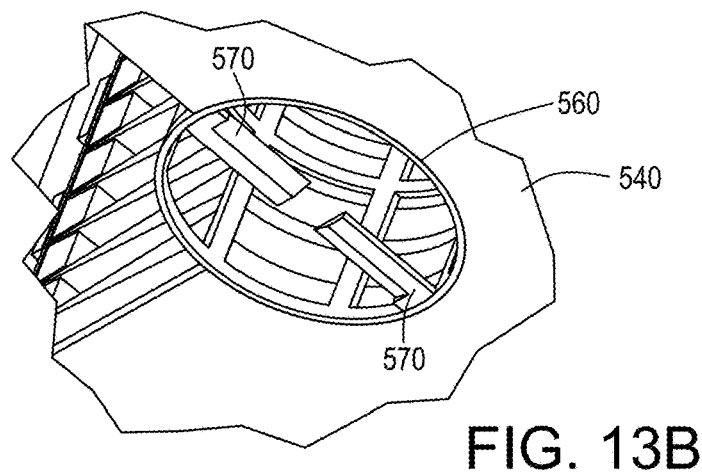
FIG. 13B illustrates a bottom of the perforated pole and choppers according to an embodiment of the invention.

FIG. 13A illustrates a filter 500, a gear 550, a perforated pole 560, choppers 570, and a filter core rotator 552 according to an embodiment of the invention. FIG. 13B illustrates an area of filter 510 that includes choppers 570. The choppers 570 are connected to an input of the perforated pole 570 so then when the perforated core is rotated the choppers chop debris that enters the filter 500 via the perforated pole 560. The input of the perforated pole 560 can be positioned directly above an opening such as fluid opening 117 of FIG. 5B Choppers 570 are shown as having fin like shape and are facing each other. There may be one or more choppers. Different choppers 570 can have different shapes and/or sizes.

The choppers can be connected to the filter core or other parts of the filter. Choppers can be positioned at different heights of the perforated pole or filter.

The choppers may be attached as propellers to axle 558.

Figure 14:
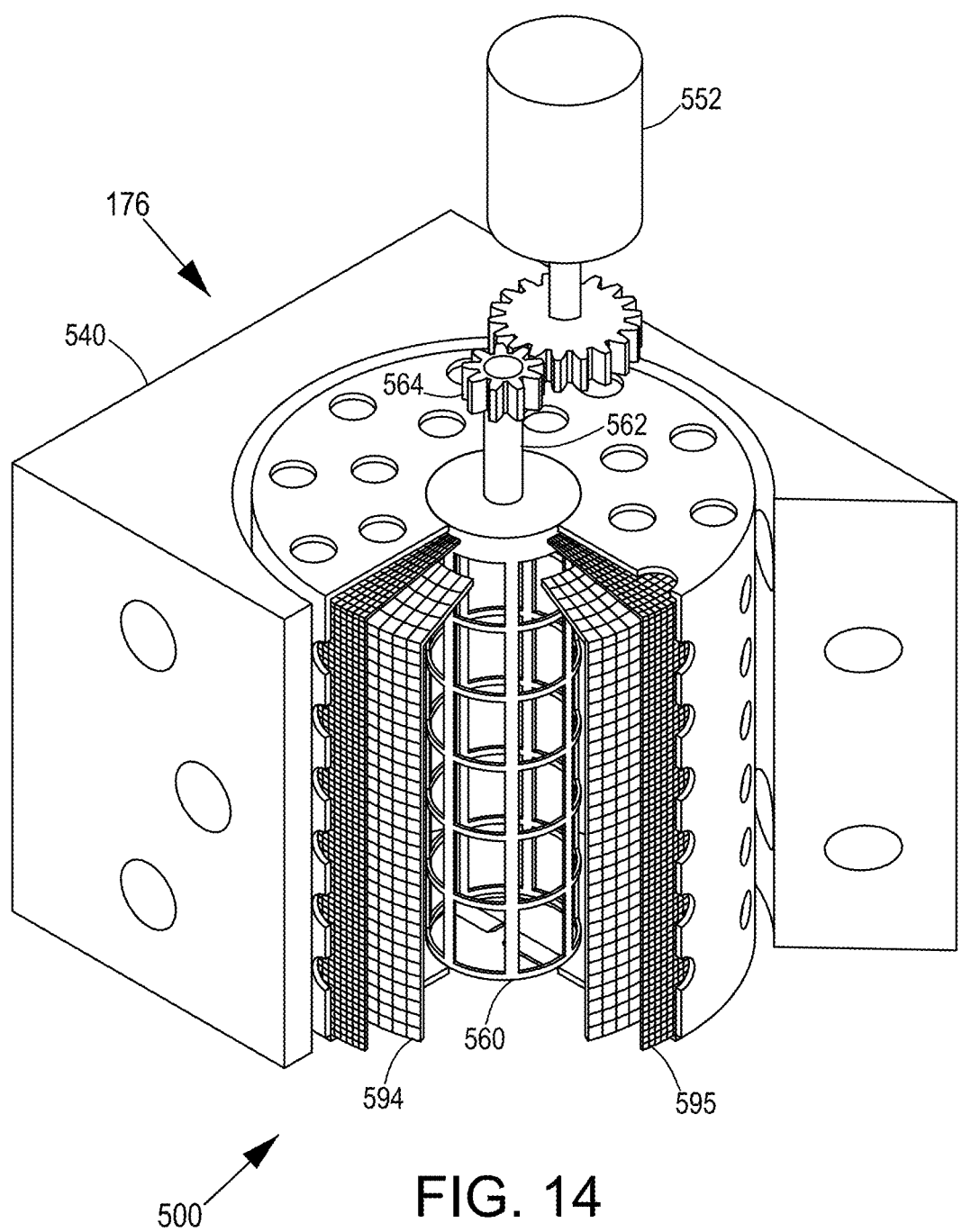
FIG. 14 illustrates a filter having a filter core that includes a fine filtering element and a coarse filtering element, a gear, a perforated pole, and a filter core rotator according to an embodiment of the invention.

FIG. 14 illustrates filter 500 as having (or being connected to) a perforated pole 560 that is connected to axel 562 that has a gear 564 at its top. Gear 564 is rotated by another gear 554 connected to filter core rotator 552. The filter core 510 includes filtering elements that are a fine filter element 595 and a coarse (or gross) filtering element 594 both are illustrated as being a cylindrical shaped meshes. Fluid from the one or more inlets of the filter are filtered by the gross filtering element 594 before being filtered by the fine filtering element 595. The gross and fine filtering elements by differ from each other by the size of particles they block. The gross filtering mesh may be constructed of 200 microns pore size and the fine mesh may be of 50 microns pore size. Other pore sizes can be provided.

Figure 15:
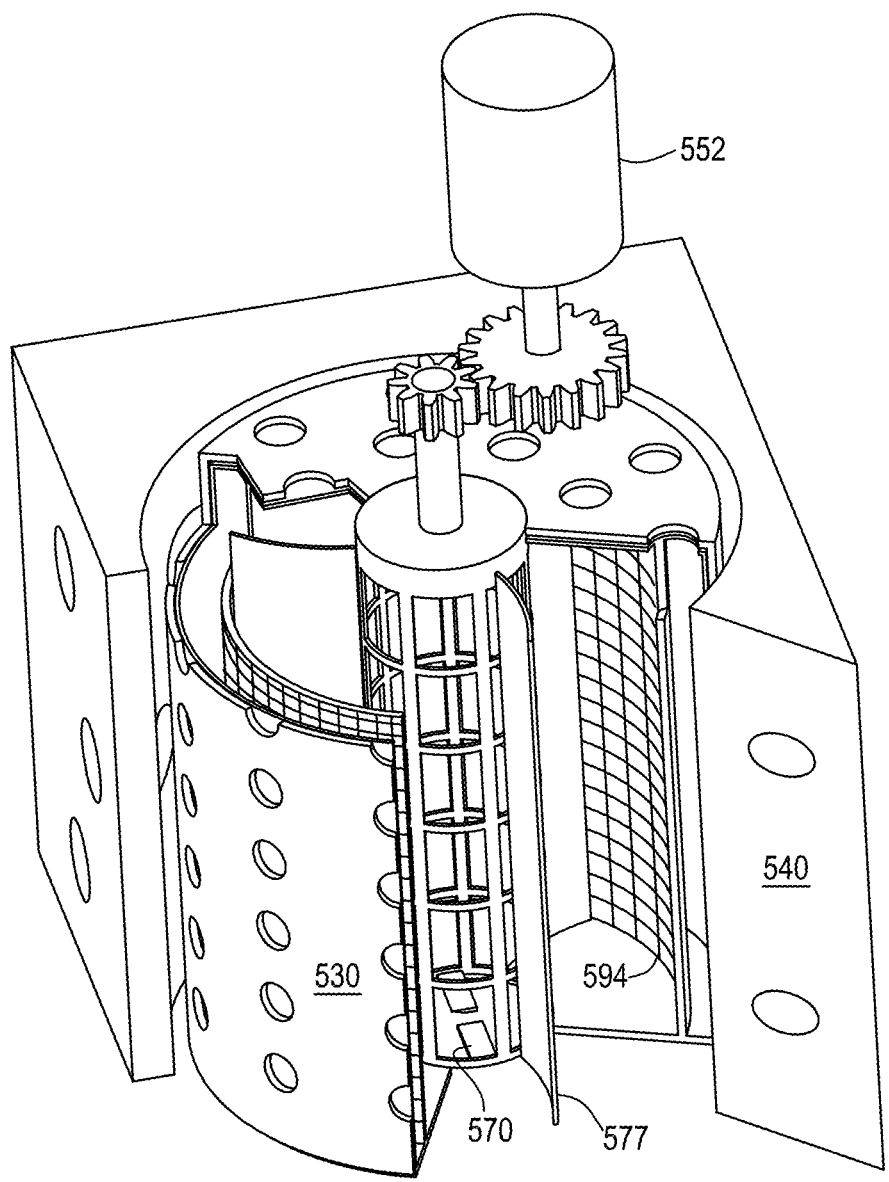
FIG. 15 illustrates a filter having a filter core that includes a filtering element and blades, a gear, a perforated pole, choppers and a filter core rotator according to an embodiment of the invention.

FIG. 15 illustrates filter 500 as having (or being connected to) a perforated pole 560 that is connected to axel 562 that has a gear 564 at its top. Gear 564 is rotated by another gear 554 connected to filter core rotator 552. The filter 500 includes blades 577 that may be connected to various other parts of the filter 510. Additionally or alternatively the blades 577 are connected to an inner cylindrical frame (not shown) that may be parallel to the perforated pole 560, may contact the perforated pole 560, may be spaced apart from the perforated pole 560, may be connected to and/or held by the filter core enclosure 530 (for example—held by the floor, bottom and/or sidewall of the filter core enclosure). When the perforated pole 560 is not connected to the blades and the filter core 510 the perforated pole 560 may remain in the pool cleaning robot after ejection of the filter core 510 and accumulated dirt can be serviced efficiently and washed off the blades. The blades 557 may extend along the entire filter enclosure 530 and are positioned between the perforated pole 560 and the filtering element 594. The blades 577 form a rotor. When the filter core 510 is rotated by filter core rotator 552 these blades may cause the filter core 510 to act as a turbine and assist the flow of water into the filter core.

Dual Mode Motor-Generator and Dual-Mode Rotor

Figure 16A:
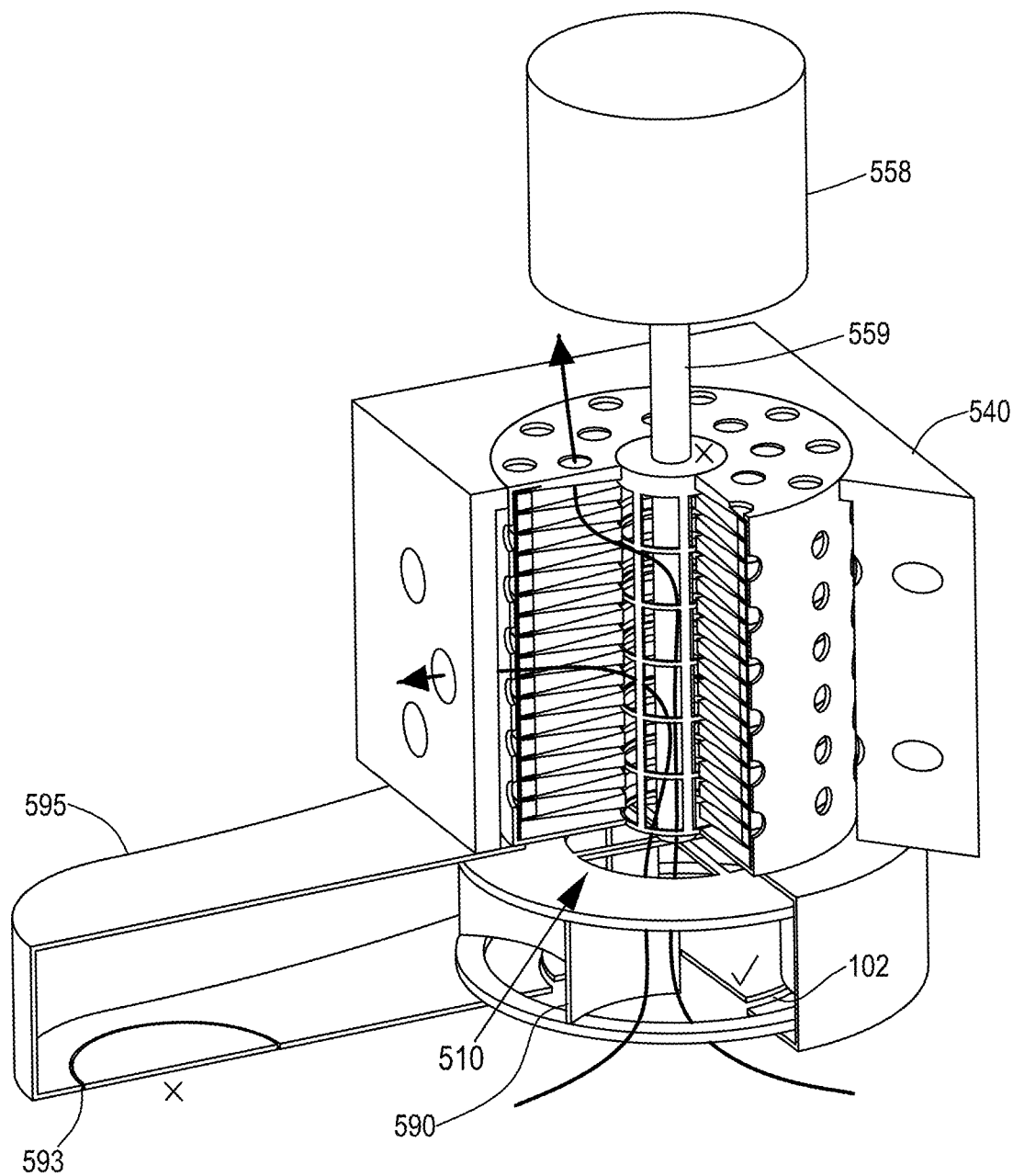
FIG. 16A illustrates a filter having a filter core that includes a zigzag shaped array of filtering elements, a perforated pole, a motor/generator that functions as a motor and acts as a filter core rotator and a turbine rotator, a rotor that acts as a turbine and is positioned below the filter and an enclosure that has a first opening below the turbine and a second opening that is selectively sealed by a uni-directional valve.
Figure 17A:
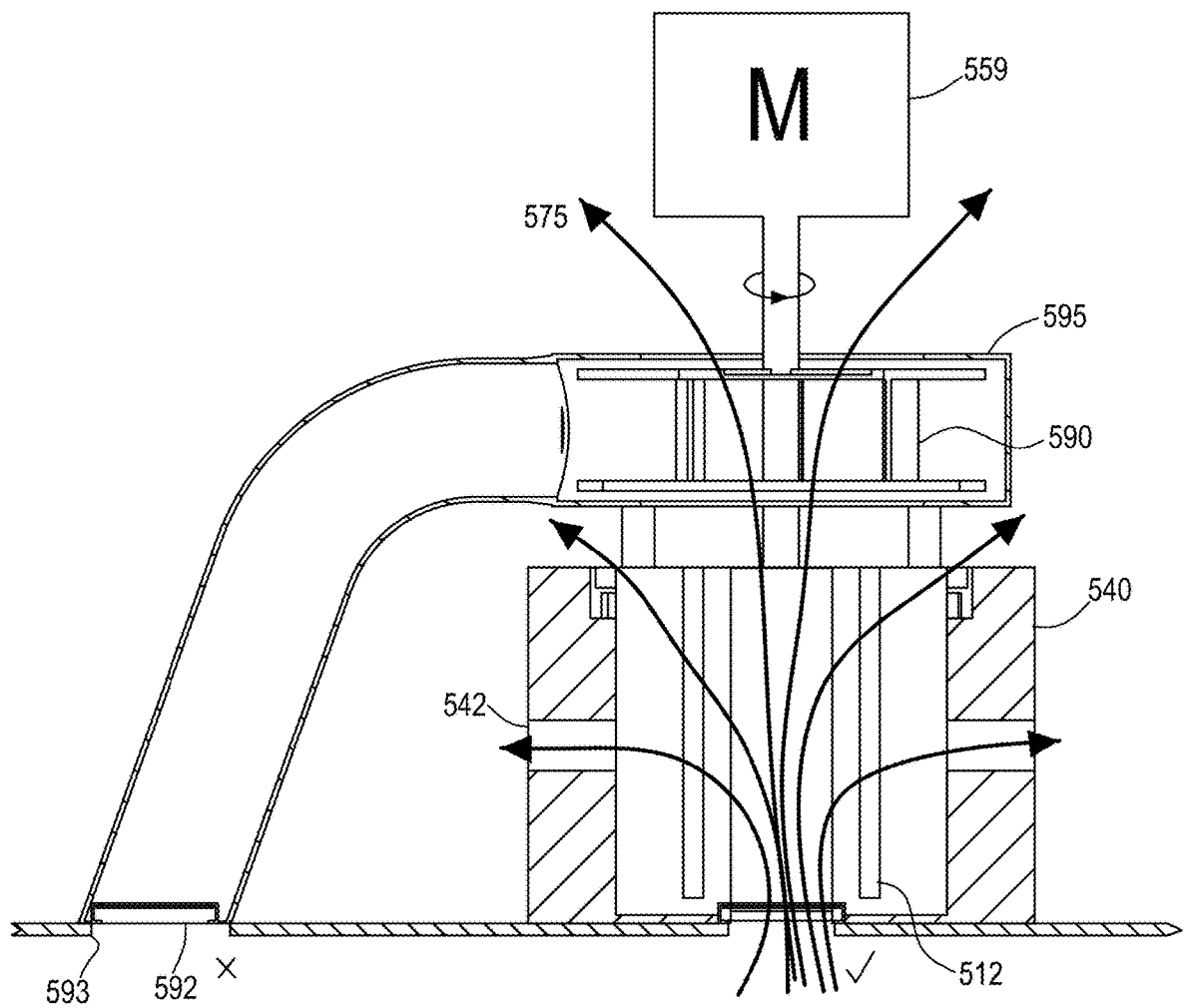
FIG. 17A is a cross sectional view of a filter having a filter core, a perforated pole, a motor/generator that functions as a motor and acts as a filter core rotator and a turbine rotator, a rotor that acts as a turbine and is positioned below the filter and an enclosure that has a first opening below the turbine and a second opening that is selectively sealed by a uni-directional valve.
Figure 17B:
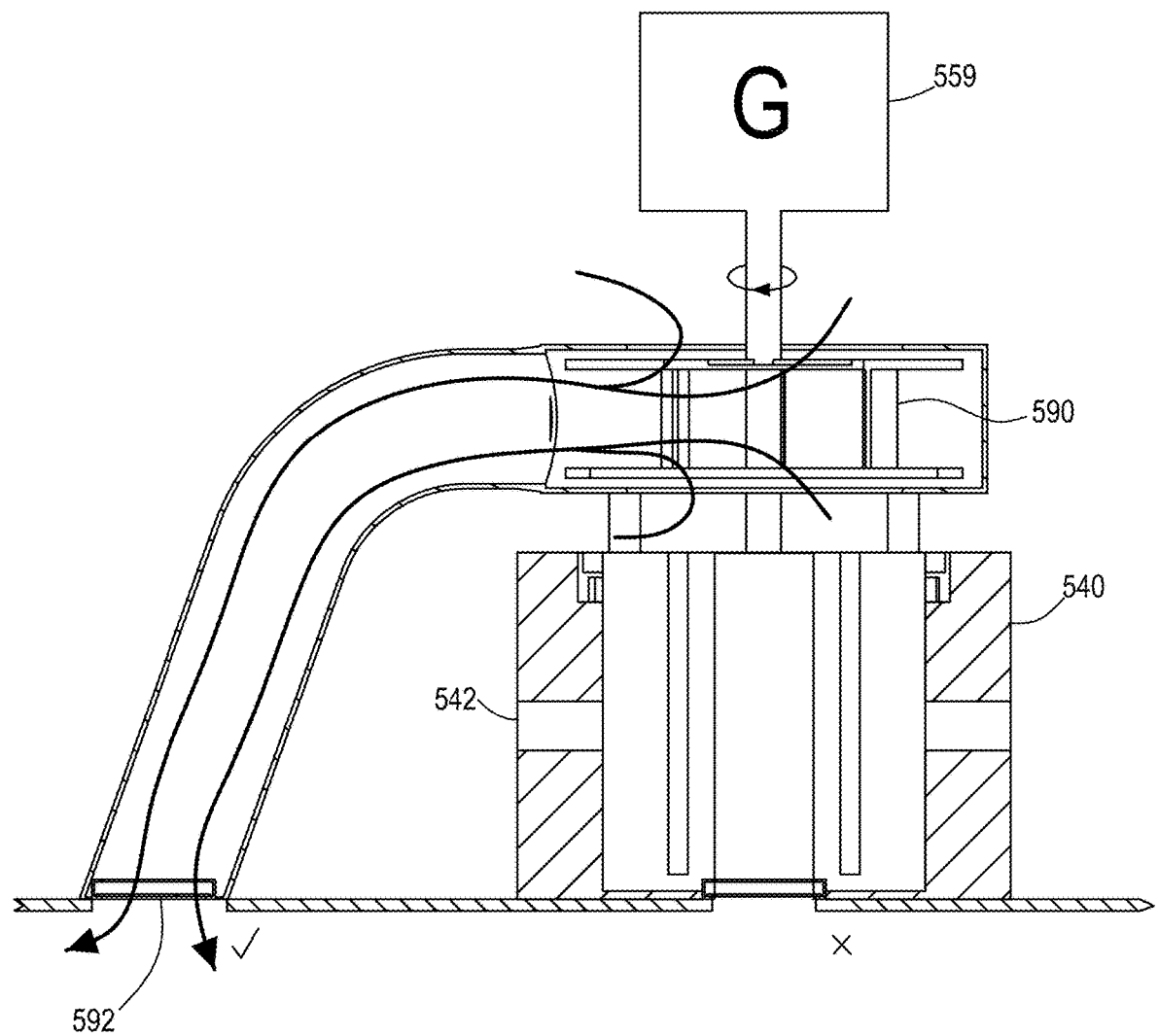
FIG. 17B is a cross sectional view of a filter having a filter core, a perforated pole, a motor/generator that functions as a generator, a rotor that acts as an impeller and is positioned below the filter and an enclosure that has a first opening below the turbine and a second opening that is selectively sealed by a uni-directional valve.
Figure 17C:
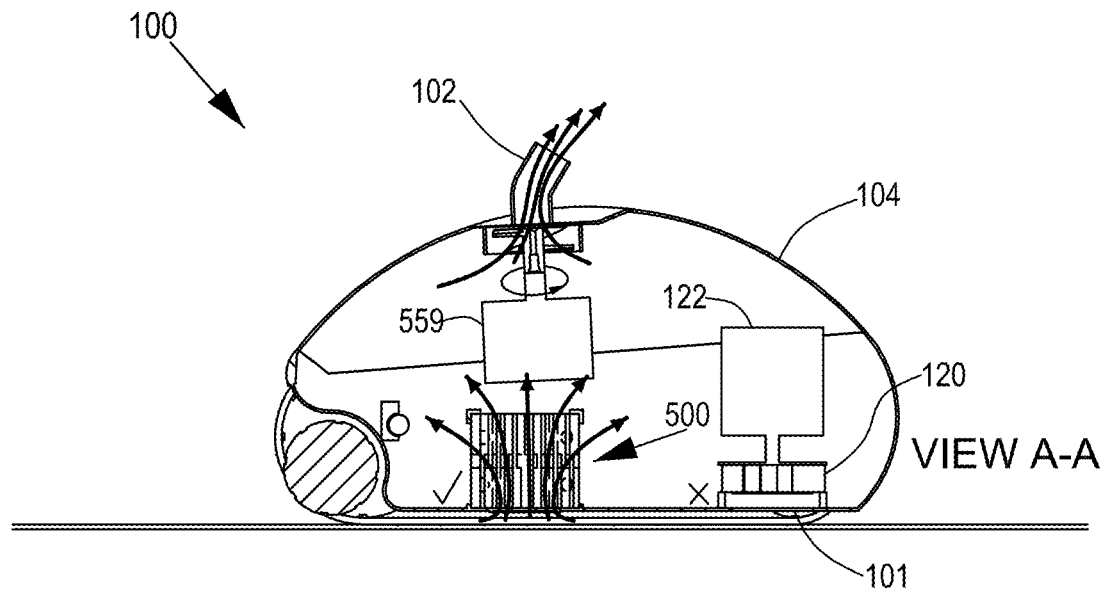
FIG. 17C is a cross sectional view of a pool cleaning robot according to an embodiment of the invention.
Figure 17D:
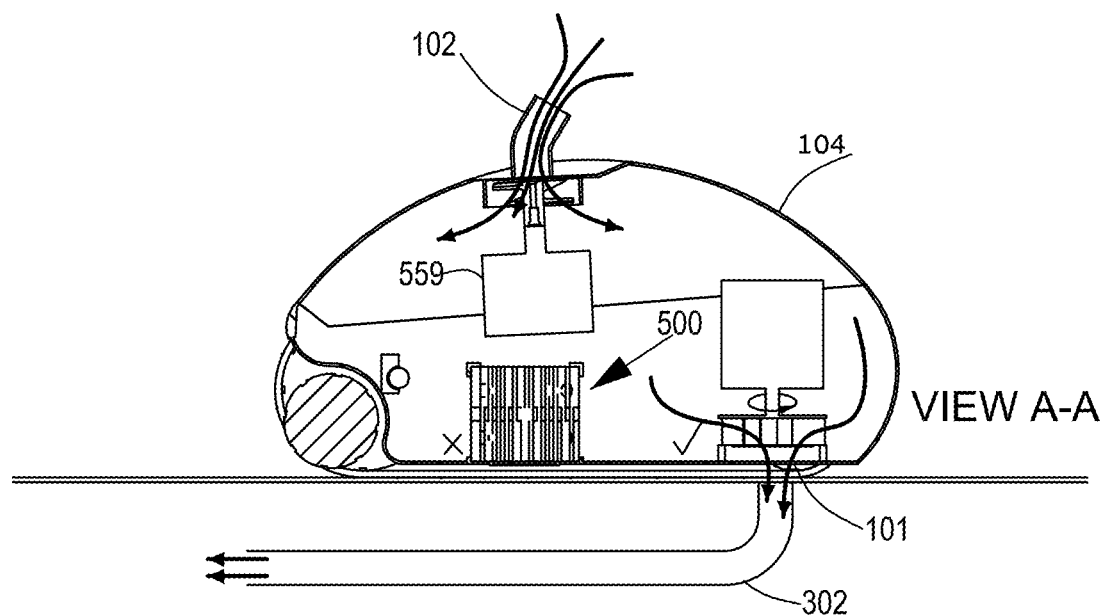
FIG. 17D is a cross sectional view of a pool cleaning robot according to an embodiment of the invention.
Figure 17E:
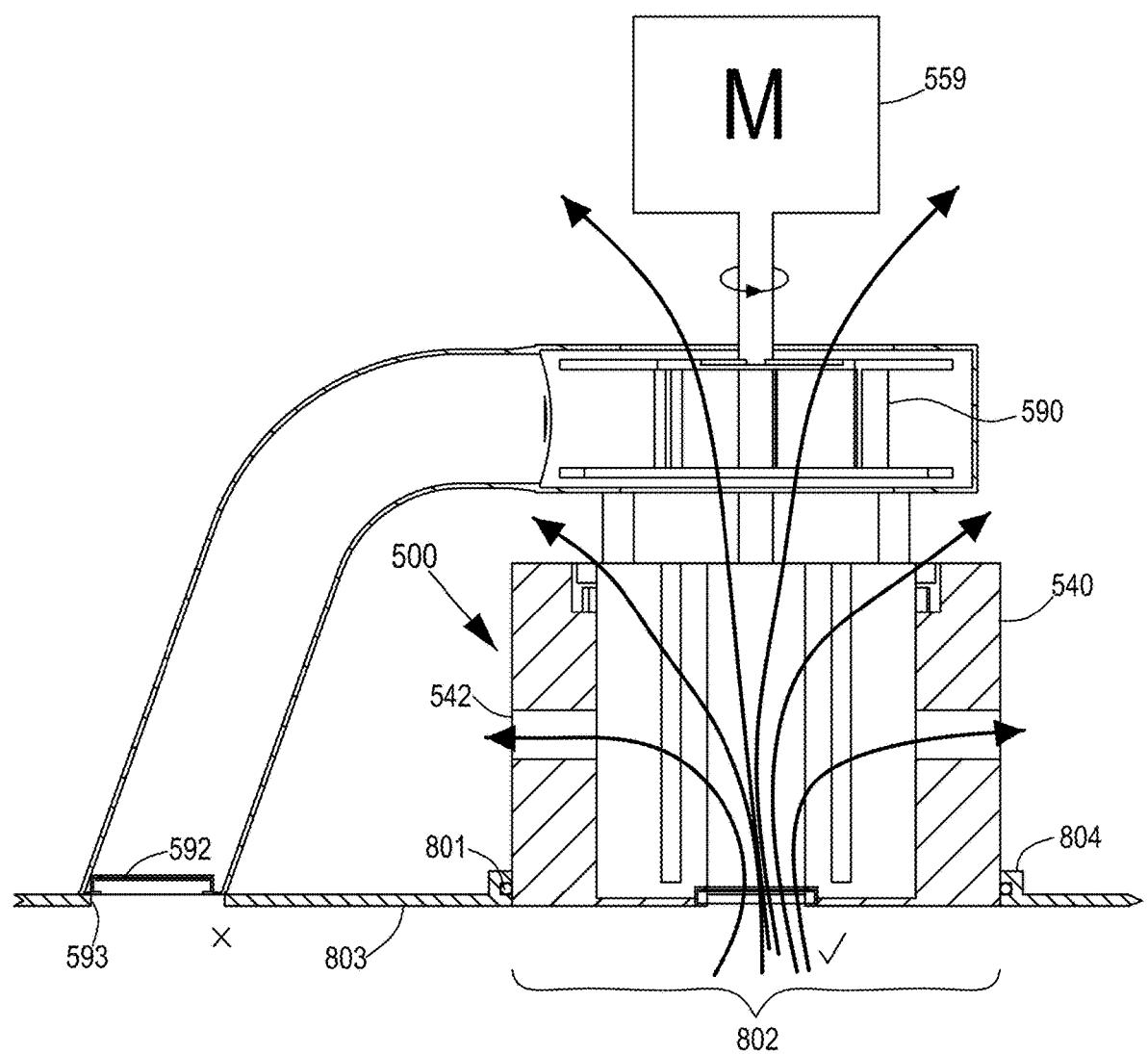
FIG. 17E is a cross sectional view of a filter having a filter core, a perforated pole, a motor/generator that functions as a motor and acts as a filter core rotator and a turbine rotator, a rotor that acts as a turbine and is positioned above the filter and an enclosure that has a first opening below the turbine and a second opening that is selectively sealed by a uni-directional valve.

FIGS. 16A, 17A and 17E illustrate a filter 500, a rotor 590 that functions as an impeller, a motor/generator 559 that functions as a motor for rotating the filter core 510 and the rotor 590, and an enclosure 595 not shown that surrounds the rotor and has (a) a first opening 102 located below the rotor 590 and (b) a second opening 593 that is selectively sealed by a uni-directional valve 592, according to an embodiment of the invention. Alternatively, the first and second openings 102 and 593 may be formed in the bottom of the pool cleaning robot 100 and the enclosure 595 may be located above the bottom in a manner that the bottom and the enclosure may provide a closed environment (except the openings 102 and 593).

In FIG. 16A the filter 500 is positioned between the rotor 590 and the motor/generator 559. In FIG. 17A the rotor 590 is positioned between the filter 500 and the motor/generator 559. An axle/spindle 558 connects the motor/generator 559 to the perforated pole 560.

In this mode of operation fluid is directed by the rotor to enter the filter 500 and to exit filter 500 after being filtered. In this mode of operation the uni-directional valve 592 seals the second opening 593.

In FIG. 17E the filter 500 (or the filter 500 and the rotor 590) can be fed to the pool cleaning robot via opening 802 formed in a bottom 803 of the pool cleaning robot. Once inserted in the pool cleaning robot connecting elements (such as elastic ring 801 placed in a space formed by connecting element 804 may hold the filter 500.

Figure 16B:
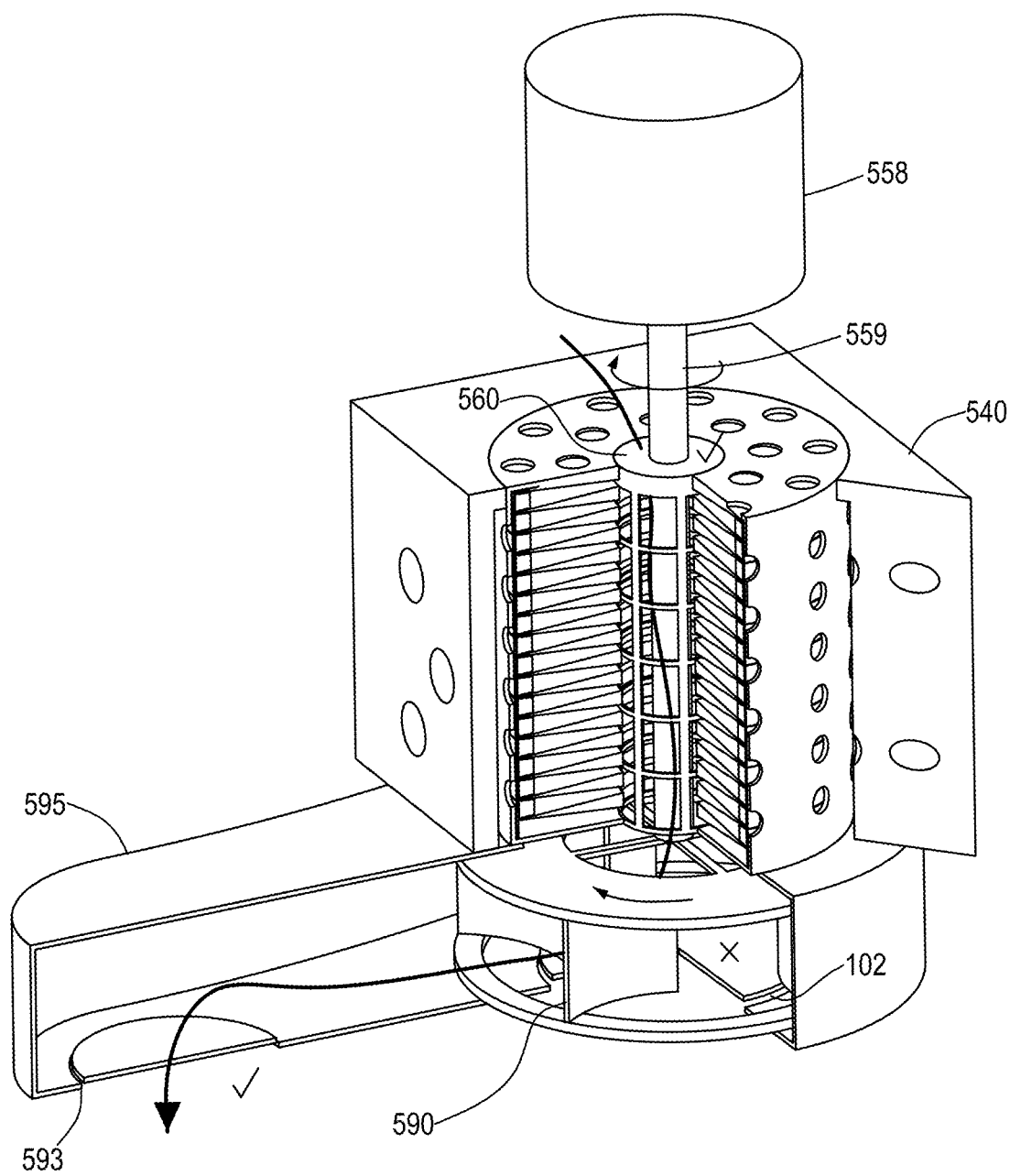
FIG. 16B illustrates a filter having a filter core that includes a zigzag shaped array of filtering elements, a perforated pole, a motor/generator that functions as a generator, a rotor that acts as an impeller and is positioned below the filter and an enclosure that has a first opening below the turbine and a second opening that is selectively sealed by a uni-directional valve.
Figure 17F:
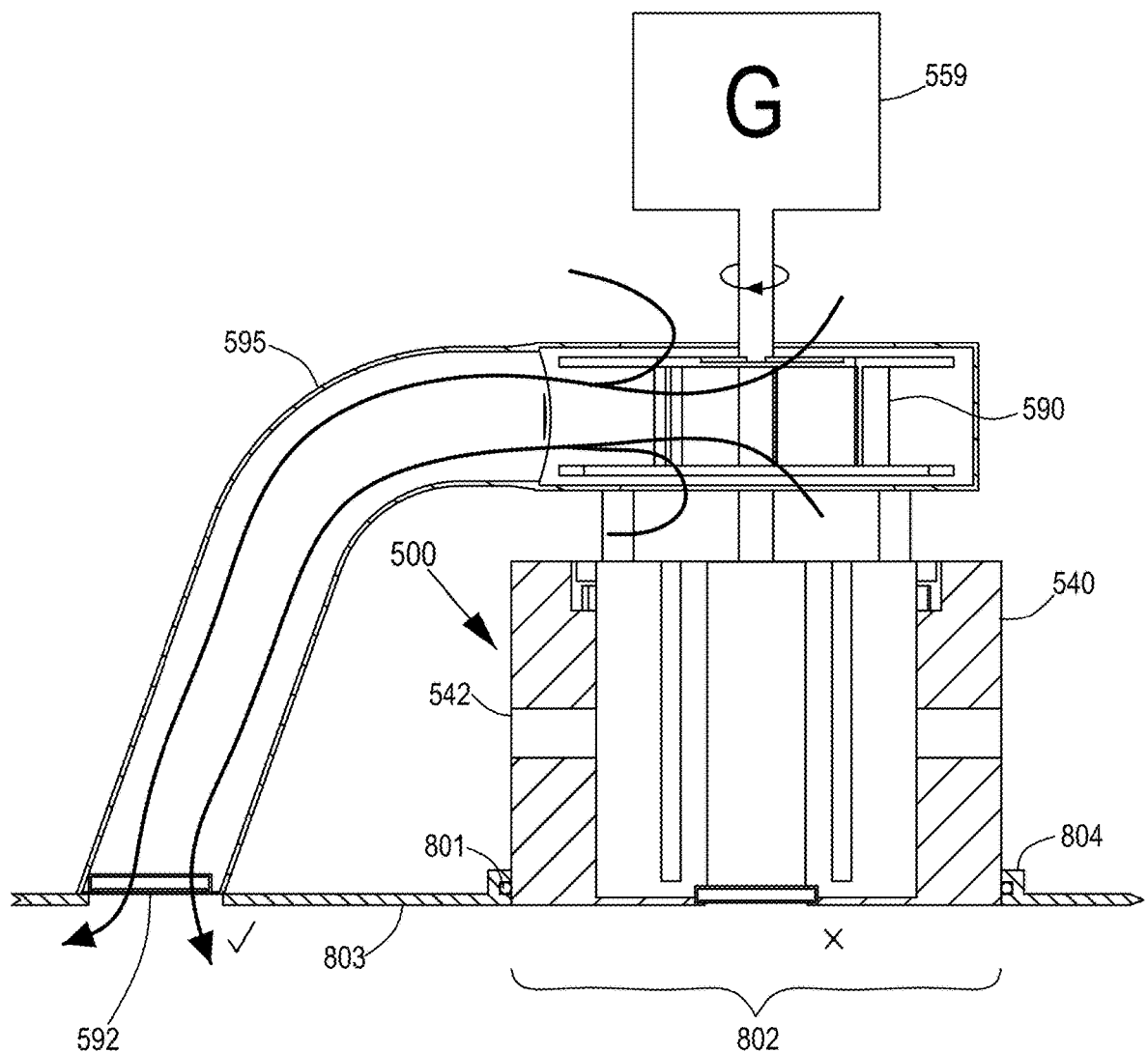
FIG. 17F is a cross sectional view of a filter having a filter core, a perforated pole, a motor/generator that functions as a generator, a rotor that acts as an impeller and is positioned above the filter and an enclosure that has a first opening below the turbine and a second opening that is selectively sealed by a uni-directional valve.

FIGS. 16B, 17B and 17F illustrate a filter 500, a rotor 590 that functions as a turbine, a motor/generator 559 that functions as a generator for generating electrical energy, and an enclosure 595 that surrounds the rotor and has a first opening 102 above the rotor 590 and a second opening 593 that is selectively sealed by a uni-directional valve 592, according to an embodiment of the invention.

Alternatively, the first and second openings 102 and 593 may be formed in the bottom of the pool cleaning robot 100 and the enclosure 595 may be located above the bottom in a manner that the bottom and the enclosure may provide a closed environment (except the openings 102 and 593).

In FIG. 16B the filter 500 is positioned between the rotor 590 and the motor/generator 559. In FIG. 17B the rotor 590 is positioned between the filter 500 and the motor/generator 559.

In this mode fluid is sucked (for example by a drain of a pool) through second opening 593 and rotates the rotor 590 that in turn rotates motor/generator 599. The uni-directional valve 592 is open.

In FIG. 17F the filter 500 (or the filter 500 and the rotor 590) can be fed to the pool cleaning robot via opening 802 formed in a bottom 803 of the pool cleaning robot. Once inserted in the pool cleaning robot connecting elements (such as elastic ring 801 placed in a space formed by connecting element 804 may hold the filter 500.

FIG. 17C is a cross sectional view of pool cleaning robot 100 according to an embodiment of the invention. The pool cleaning robot 100 includes housing 104 filter 500, a rotor 590 that functions as an impeller, a motor/generator 559 that functions as a motor for rotating the filter core (part of filter 500) and the rotor 590, electrical generator 122 and turbine 120 that are spaced apart from filter 500 and are positioned above another opening of the housing. In this mode of operation fluid is directed by the rotor 590 to enter the filter 500 and to exit filter 500 after being filtered. In this mode of operation a uni-directional valve (not shown) seals the opening below turbine 120.

FIG. 17D is a cross sectional view of pool cleaning robot 100 according to an embodiment of the invention. The pool cleaning robot 100 includes housing 104 filter 500, a rotor 590 that functions as a turbine, a motor/generator 559 that functions as an electrical generator and the rotor 590, an electrical generator 122 and turbine 120 that are spaced apart from filter 500 and are positioned above another opening of the housing. The opening below the turbine 120 is opened and fluid is sucked (for example by drain 302 of a pool) through opening 102 into the pool cleaning robot and out of the pool cleaning robot to drain 302 thereby rotating the rotor 590 that in turn rotates motor/generator 599 and rotating turbine 120.

Any one or a combination of the filter 500 and the rotor 590 of FIGS. 16A, 16B, 17A, 17B, 17C, 17D, 17E and 17F can be replaced underwater (or above the water) through openings formed in the pool cleaning robot. This is illustrated by opening 802 formed in the bottom of the housing in FIGS. 17E and 17F. The opening can be formed in sidewall of the pool cleaning robot. When any filter is provided into the pool cleaning robot (for example, any one of the filters illustrated in FIGS. 5A, 5C, 6A, 6B, 7A, 7B, 7C, 7D, 12, 17E and 17F) it can be held to its position by any known fastening or holding element known in the art such as pins, blots, stripes, rails, springs and the like. Additionally or alternatively the opening through which the filter is inserted can close or at least partially close the opening through which the filter entered. For example, after a filter has been inserted from the bottom of the pool cleaning robot, it may be fastened by vertical elements that contact the upper part of the filter, the filter opening may close, the filter can be inserted into vertical or otherwise erect rails and the like.

Figure 18A:
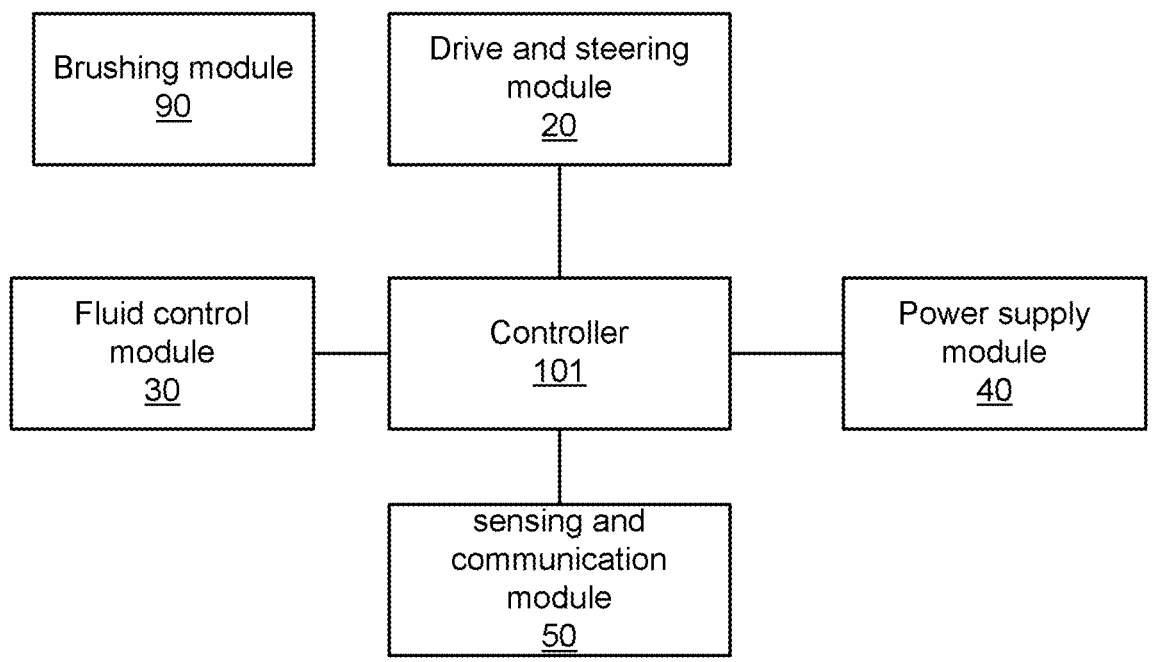
FIG. 18A illustrates various components of a pool cleaning robot according to an embodiment of the invention.

FIG. 18A illustrates various components of a pool cleaning robot 100 according to an embodiment of the invention.

The pool cleaning robot 100 is illustrated as including controller 101, drive and steering module 20, power supply module 40, fluid control module 30, sensing and communication module 50 and brushing module 90.

The controller 101 is arranged to control the operation of the pool cleaning robot 100 and especially control the various modules 20, 30, 40 and 50. For example, the controller 101 may be arranged to navigate the pool cleaning robot 100 to direct the pool cleaning robot to be positioned in a certain location in which a flow level of fluid that is circulated by a pool fluid circulation system is higher than a flow level of the fluid within a majority of the pool (for example—to be in proximity to a drain of the pool), wherein when positioned at the certain location the fluid that is circulated by a pool fluid circulation system passes through a fluid path formed in the pool cleaning robot and thereby rotate a turbine.

Figure 18B:
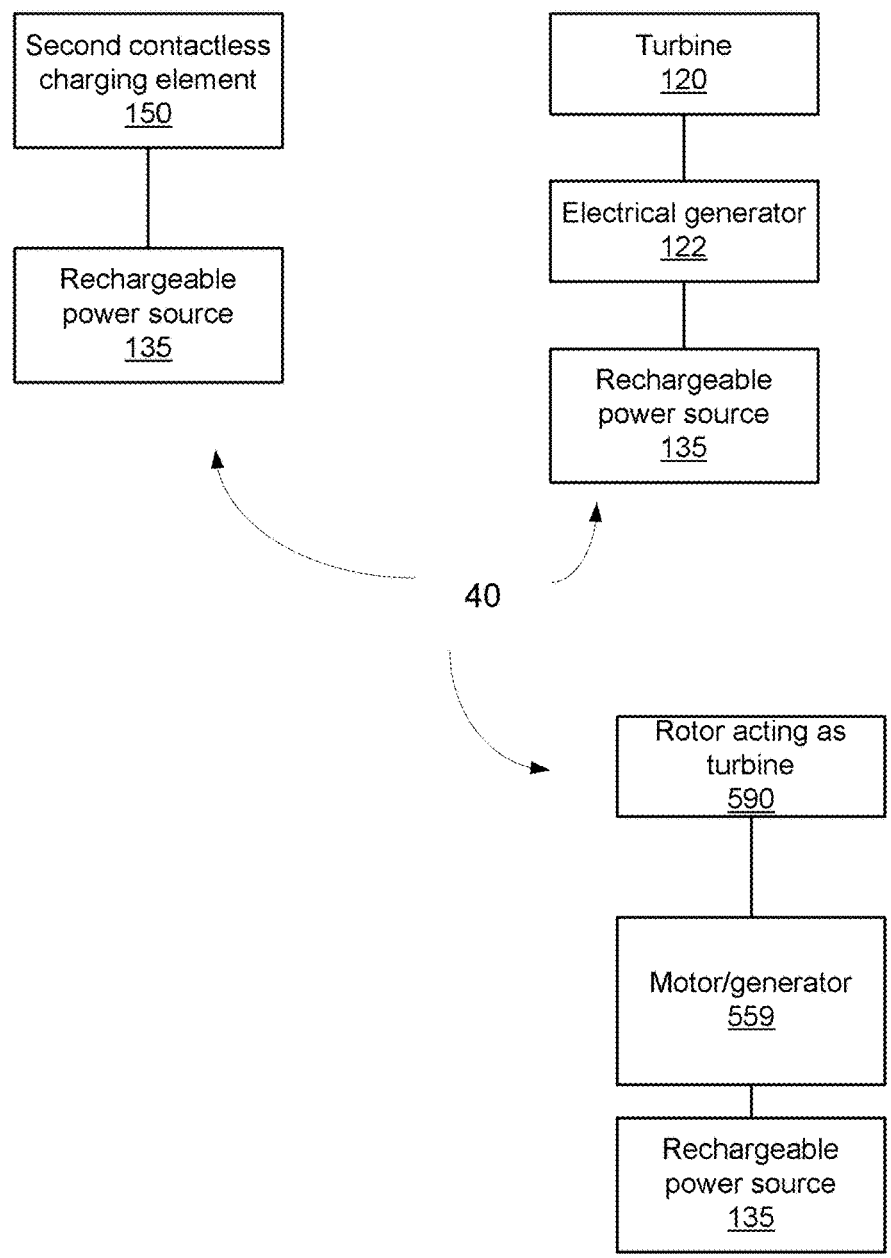
FIG. 18B illustrates power supply modules of a pool cleaning robot according to various embodiments of the invention.

FIG. 18B illustrates power supply modules 40 of a pool cleaning robot 100 according to various embodiments of the invention.

The power supply module 40 is configured to provide electrical power to various power consuming components such as controller 101, motors, sensors, and the like. It may receive the electrical power or generate it.

One power supply module 40 includes a second contactless charging element 150 and a rechargeable power source 135 (see, for example FIGS. 3A-3B and 4A-4C).

Another power supply module 40 includes a turbine 120, electrical generator 122 and a rechargeable power source 135 (see, for example FIGS. 2A-2C).

A further power supply module 40 includes a rotor 590 that acts as a turbine, a motor/generator 559 that acts as a generator and a rechargeable power source 135 (see, for example FIGS. 16A-16B and 17A-17B).

Figure 18C:
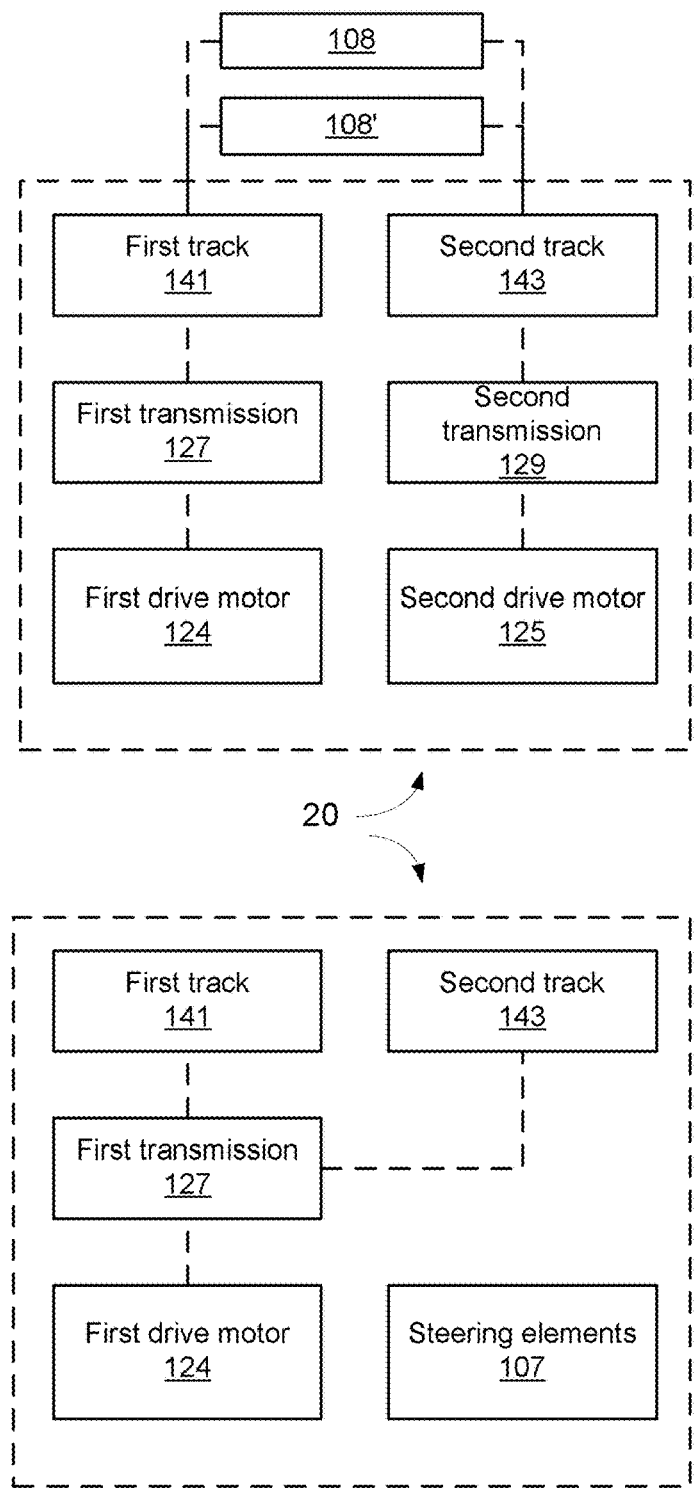
FIG. 18C illustrates drive and steering modules a pool cleaning robot according to various embodiments of the invention.

FIG. 18C illustrates drive and steering modules 20 of a pool cleaning robot according to various embodiments of the invention.

Drive and steering module 20 is arranged to move the pool cleaning robot 100. It may include one or more motors, one or more wheels or tracks and one or more transmissions that convey movements introduced by motors to the one or more wheels and/or one or more tracks.

One drive and steering module 20 includes first drive motor 124, second drive motor 125, first transmission 127, second transmission 129, first track 141 and second track 143. Some of these components are shown in FIGS. 1, 2A-2C, 3A-3C, 4A-4B and the like.

The pool cleaning robot 100 may include a brushing module (denoted 90 in FIG. 18A) that may include one or more brushing wheels such as brushing wheels 108 that are rotated (directly or indirectly) by first and second tracks 141 and 143. The direction of movement of the pool cleaning robot 100 can be controlled by individually controlling the movement of first and second tracks 141 and 143.

Another drive and steering module 20 includes first drive motor 124, first transmission 127, first track 141, second track 143, brushing wheels (not shown) and steering elements 107. Steering elements 107 can include fins, imbalance introduction elements, controllable fluid jet elements and the like. Non-limiting examples of steering elements are provided in U.S. patent application Ser. No. 14/023,544 filed Sep. 11, 2013 which is incorporated herein by reference. Any other steering elements known in the art can be used.

Figure 18D:
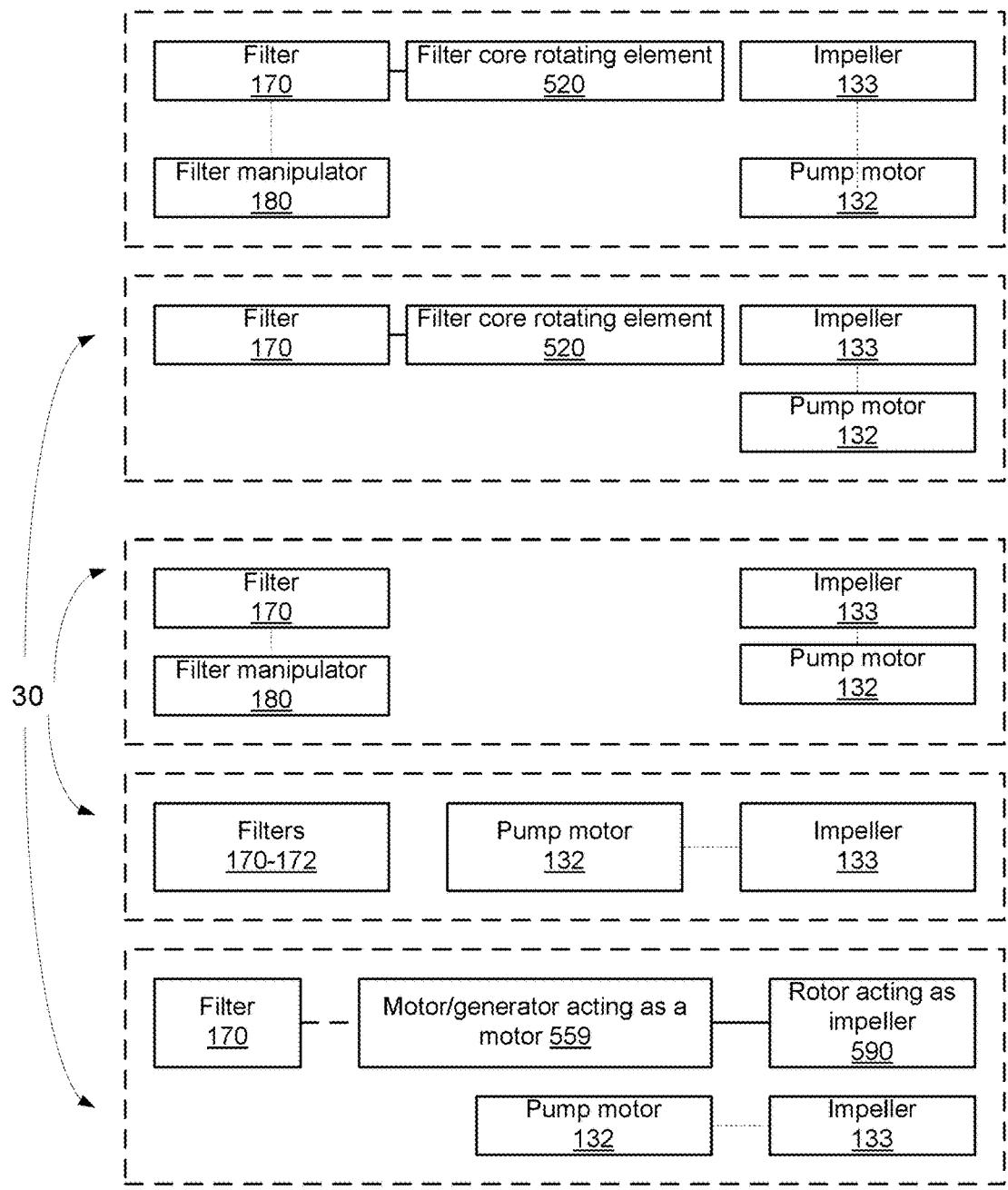
FIG. 18D illustrates fluid control modules of a pool cleaning robot according to various embodiments of the invention.

FIG. 18D illustrates fluid control modules 30 of a pool cleaning robot according to various embodiments of the invention.

A fluid control module 30 is arranged to control a flow of fluid within the pool cleaning robot and to filter said fluid.

It may include, any combination of the following:

a. Impeller 133 and pump motor 132 for inducing fluid to flow through the pool cleaning robot 100 (see, for example FIG. 2C).
b. Rotor 590 that acts as an impeller and a motor/generator 559 that acts as a motor (see, for example, FIGS. 16A, 16B, 17A, 17B, 17C, 17D).
c. Filter 170, 172, 174 or 500. The filter may have, for example, a filter core 510, a filter enclosure 530 and a filter housing 540.
d. A filter core rotating element 552 (see, for example, FIGS. 10, 12 and 14).
e. Filter manipulator 180 (see, for example, FIG. 8).
a. Impeller 133 and pump motor 132 for inducing fluid to flow through the pool cleaning robot 100 (see, for example FIG. 2C). b. Rotor 590 that acts as an impeller and a motor/generator 559 that acts as a motor (see, for example, FIGS. 16A, 16B, 17A, 17B, 17C, 17D). c. Filter 170, 172, 174 or 500. The filter may have, for example, a filter core 510, a filter enclosure 530 and a filter housing 540. d. A filter core rotating element 552 (see, for example, FIGS. 10, 12 and 14). e. Filter manipulator 180 (see, for example, FIG. 8).

Figure 18E:
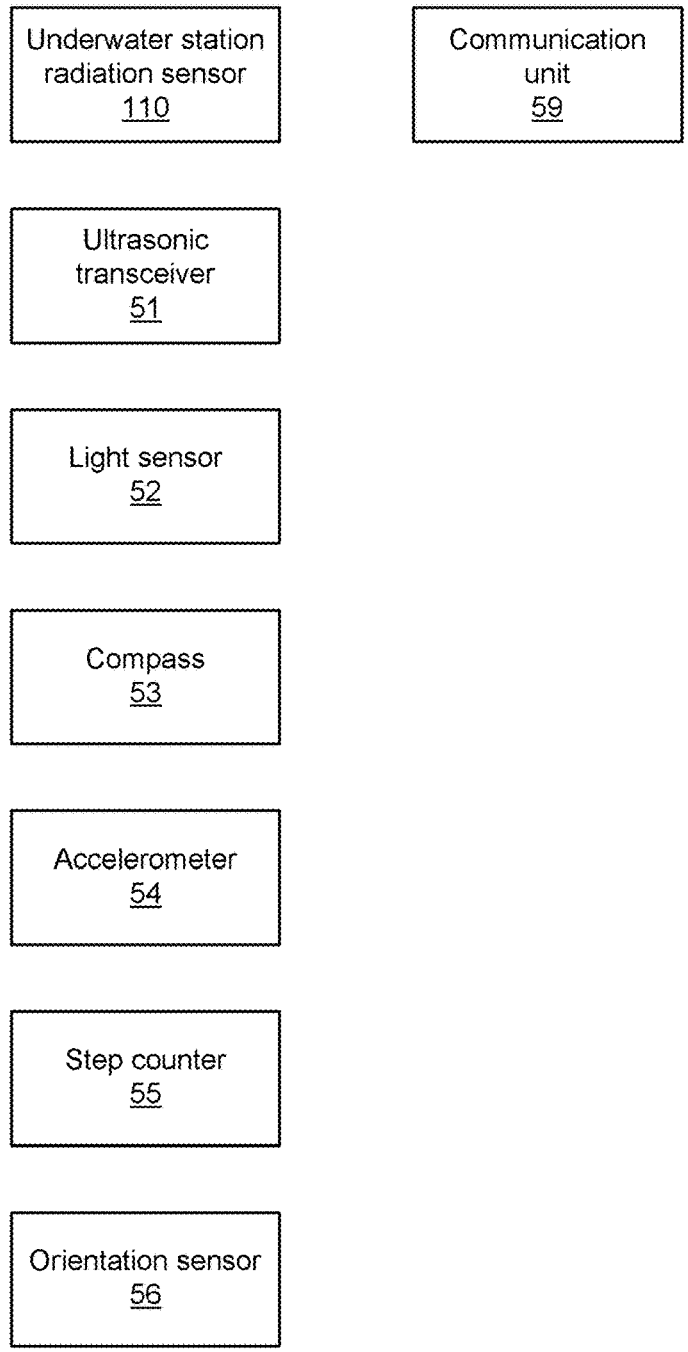
FIG. 18E illustrates sensors of a sensing and communication module of a pool cleaning robot according to various embodiments of the invention.

FIG. 18E illustrates sensors of a sensing and communication module 50 of a pool cleaning robot according to various embodiments of the invention. The sensing and communication module 50 may include one or more of the following sensors:

a. Underwater station radiation sensor 110 for sensing radiation from an underwater station (see, FIG. 1).
b. Ultrasonic transceiver 51 for sensing a flow of fluid in the pool—that is expected to be relatively high near the drain of other flow inducing elements of a pool fluid circulation system.
c. Acoustic sensor 52 that may include an acoustic emitter and an acoustic detector to provide information about the area of the pool the pool cleaning robot 100 is passing on.
d. Gyrocompass 53 or multiple gyrocompasses for providing directional information.
e. Accelerometer 54.
f. Step counter 56 for measuring movement of the pool cleaning robot.
g. Orientation sensor 56 for sensing the orientation of the pool cleaning robot 100.
h. Communication unit 59 for communication with the underwater station 200, or with other elements in the pool (see element 306 of FIG. 2A) or outside the pool.
a. Underwater station radiation sensor 110 for sensing radiation from an underwater station (see, FIG. 1). b. Ultrasonic transceiver 51 for sensing a flow of fluid in the pool—that is expected to be relatively high near the drain of other flow inducing elements of a pool fluid circulation system. c. Acoustic sensor 52 that may include an acoustic emitter and an acoustic detector to provide information about the area of the pool the pool cleaning robot 100 is passing on. d. Gyrocompass 53 or multiple gyrocompasses for providing directional information. e. Accelerometer 54. f. Step counter 56 for measuring movement of the pool cleaning robot. g. Orientation sensor 56 for sensing the orientation of the pool cleaning robot 100. h. Communication unit 59 for communication with the underwater station 200, or with other elements in the pool (see element 306 of FIG. 2A) or outside the pool.

Figure 18F:
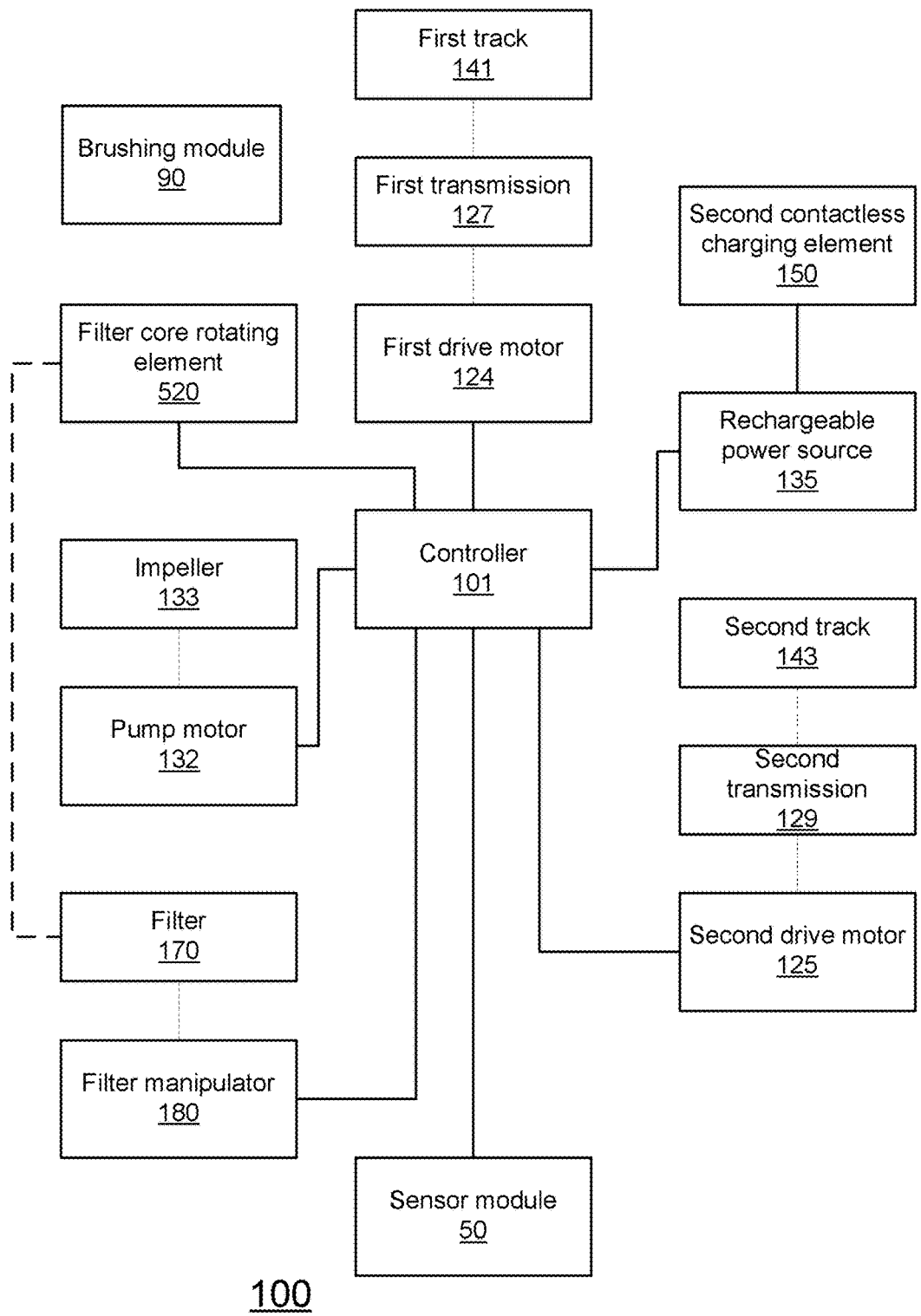
FIG. 18F illustrates various components of a pool cleaning robot according to an embodiment of the invention.

FIG. 18F illustrates various components of a pool cleaning robot 100 according to an embodiment of the invention. This is an example of combination of controller 101 and various components of the drive and steering module 20, power supply module 40, fluid control module 30, sensing and communication module 50 and brushing module 90.

In FIG. 18F the pool cleaning robot 100 includes controller 101, sensing and communication module 50, filter 170, filter manipulator 180, filter core rotating element 520, rechargeable power source 135, second contactless charging element 150, impeller 133, pump motor 132, first and second drive motors 124 and 125, first and second transmissions 127 and 129, first and second tracks 141 and 143.

Figure 18G:
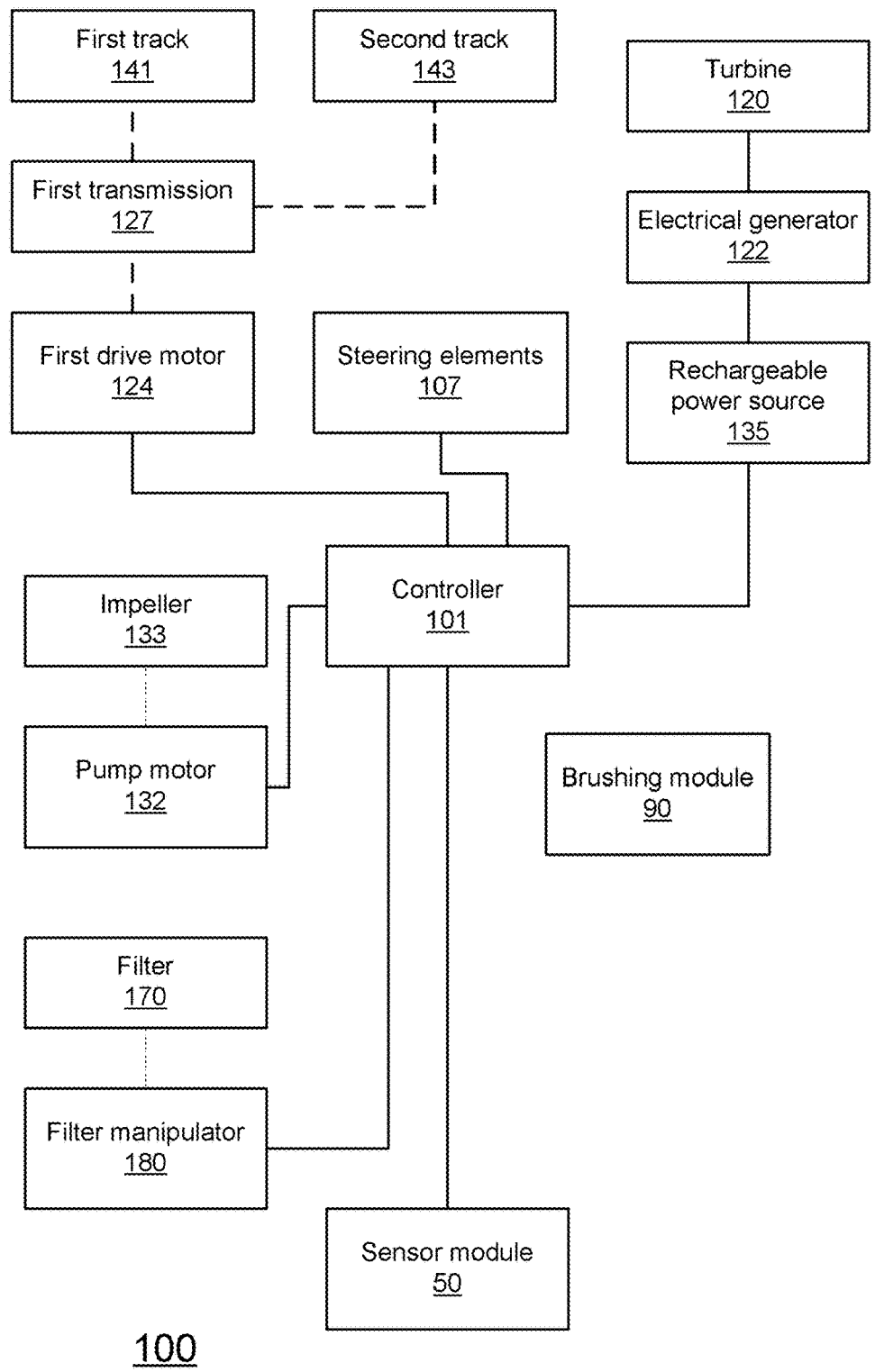
FIG. 18G illustrates various components of a pool cleaning robot according to an embodiment of the invention.

FIG. 18G illustrates various components of a pool cleaning robot 100 according to an embodiment of the invention.

In FIG. 18G the pool cleaning robot 100 includes controller 101, sensing and communication module 50, filter 170, filter manipulator 180, rechargeable power source 135, electrical generator 122, turbine 120, impeller 133, pump motor 132, first drive motor 124, steering elements 107, first transmission 127, first and second tracks 141 and 143 and brushing module 90.

Figure 18H:
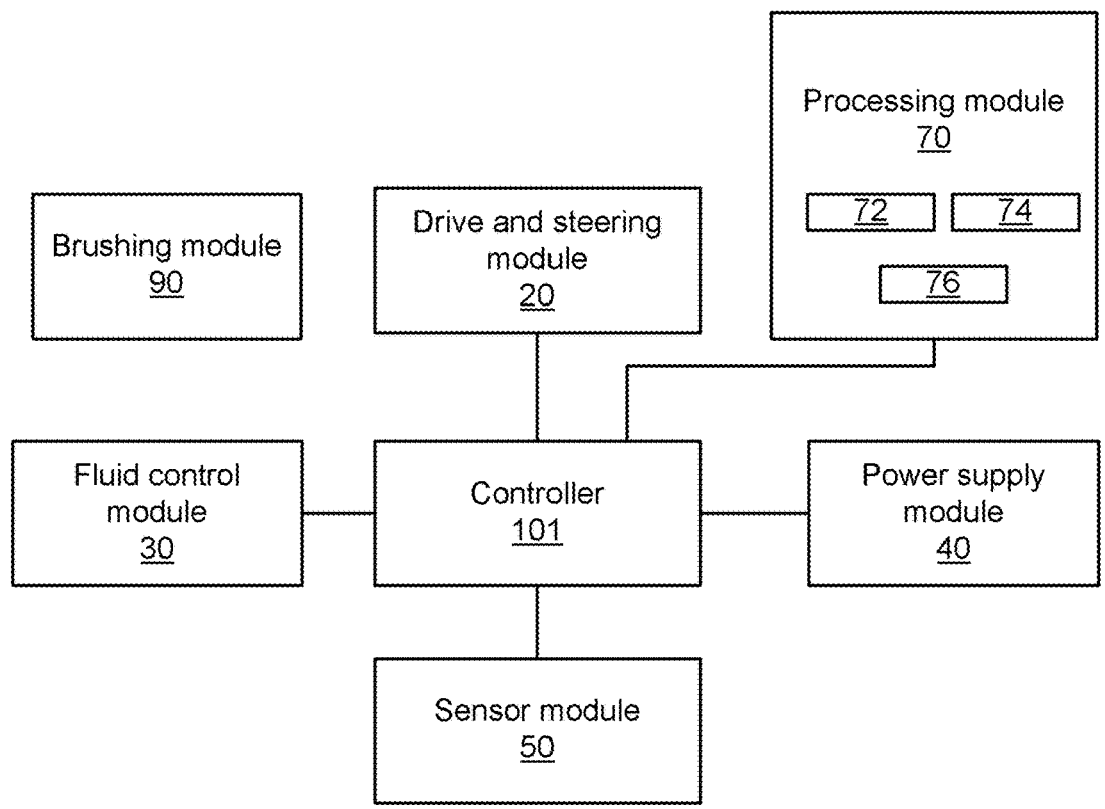
FIG. 18H illustrates various components of a pool cleaning robot according to an embodiment of the invention.

FIG. 18H illustrates various components of a pool cleaning robot 100 according to an embodiment of the invention.

This is an example of combination of controller 101, drive and steering module 20, power supply module 40, fluid control module 30, sensing and communication module 50, brushing module 90 and a processing module 70. The processing module 70 is arranged to process filters (not shown). The processing module 70 may include at least one out of: sanitizing unit 72 that is arranged to irradiate a filter with ultraviolet radiation or perform any other sanitizing process, compressor 74 for compressing a used filter (for example—filter 174 of FIG. 5A), a shredder 76 for shredding a user filter a portion of the filter (its core), and a float inducing module 78 for attaching a floating material (foam, balloon that is inflated) to a user filter and the like.

The processing module 70 can be part of any of the pool cleaning robots illustrated in any previous figures or in any other text of the specification.

Figure 19A:
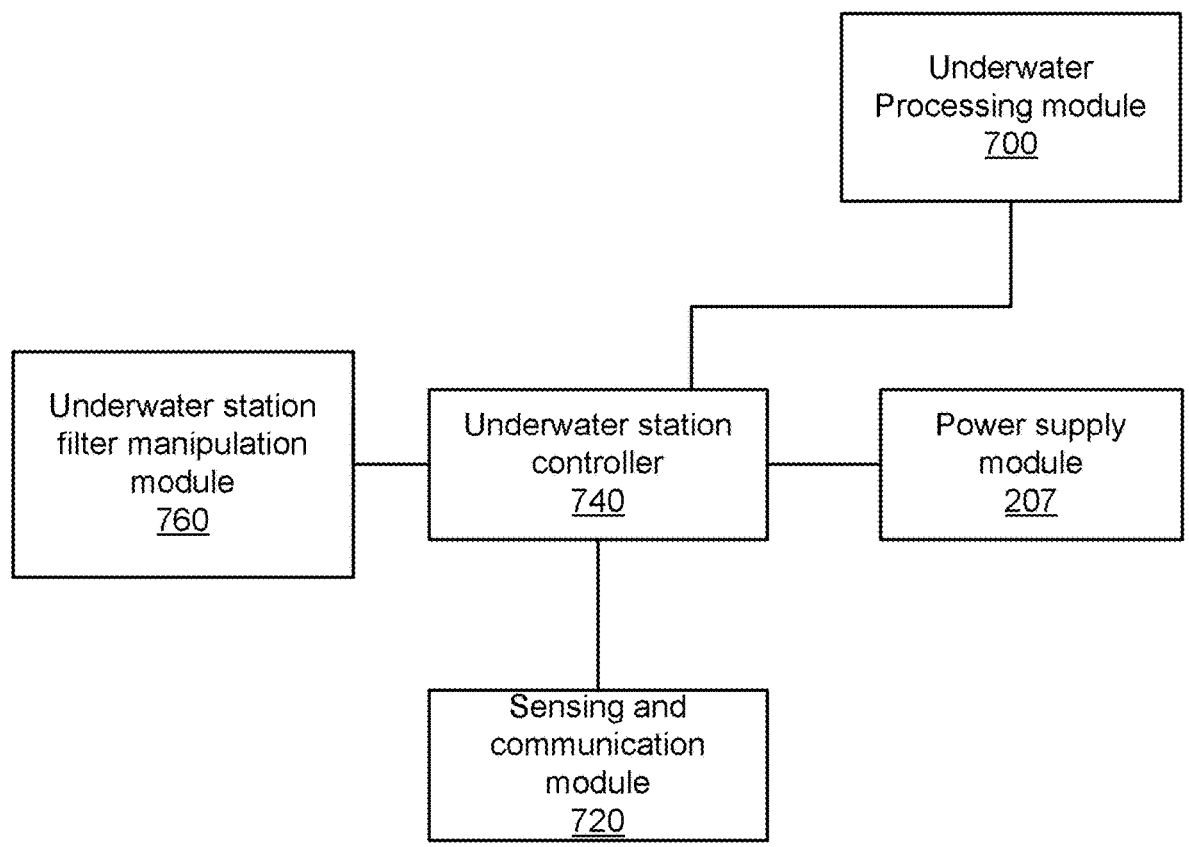
FIG. 19A illustrates various components of an underwater station according to an embodiment of the invention.

FIG. 19A illustrates various components of an underwater station 200 according to an embodiment of the invention.

The underwater station 200 includes an underwater station controller 740, an underwater station filter manipulation module 760, a sensing and communication module 720, a power supply module 207, and an underwater processing module 700.

The underwater station controller 740 controls the various modules of the underwater station 200. It can, for example, use information from sensing and communication module 720 for sensing when a pool cleaning robot is positioned within a charging range from a first contactless charging element and control a provision of power to said first contactless charging element. It may initiate, control and stop a filter insertion process to a pool cleaning robot and/or a filter ejection process from a pool cleaning robot and the like.

The sensing and communication module 720 may include one or more sensors for sensing the location of the pool cleaning robot 100, the status of various operations (processing filters, feeding or extracting filters) and the like. This information may be fed to the underwater station controller 740. This module communicates with the pool cleaning robot or other devices in or outside the pool.

The power supply module 207 supplies power to the various modules of the underwater station 200 and may also feed (in a contactless or a contact based manner) a pool cleaning robot.

The underwater processing module 700 may perform at least one out of: sanitizing of pre-used or used filters, compressing used filters, shredding user filters attaching a floating material (foam, balloon that is inflated) to a user filters and the like.

Figure 19B:
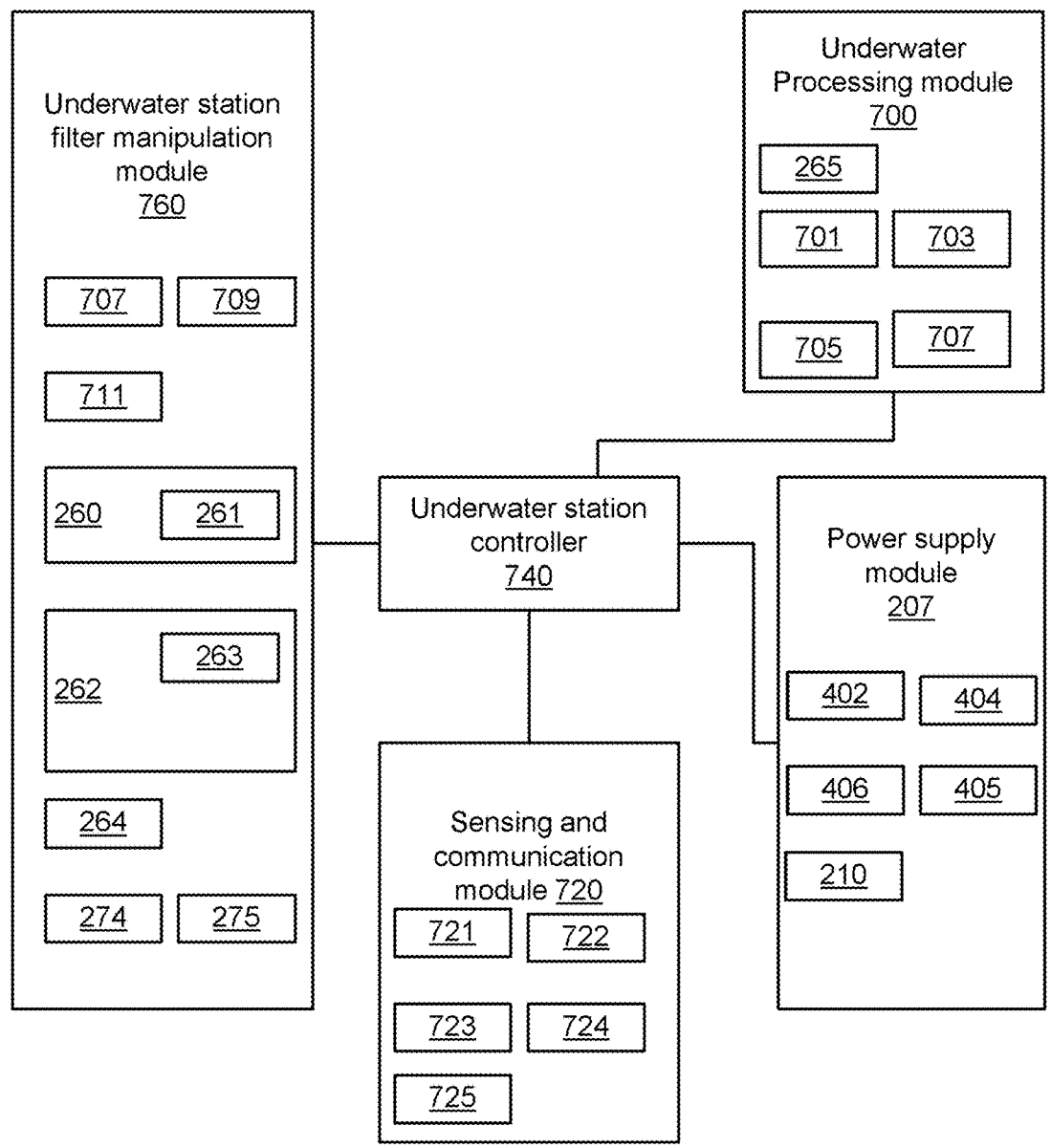
FIG. 19B illustrates various components of an underwater station according to an embodiment of the invention.

FIG. 19B illustrates various components of an underwater station 200 according to an embodiment of the invention. This figure illustrates multiple components per each module of the underwater station 200. Any combination of any components can be provided.

The underwater station filter manipulation module 760 may include at least one out of
a. In-housing manipulator 711 for manipulating filters within housing 250.
  i. Filter manipulator 260 is arranged to store and manipulate pre-used filters (including inserting the pre-used filters to a pool cleaning robot 100, providing and/or arranging filters to/within filter storage module 272, ejecting filters from a pool cleaning robot (see, arm 261 of FIGS. 6A and 6B).
  ii. Filter manipulator 262 is arranged to store and manipulate used-filters (extract from pool cleaning robot, direct used filter towards housing and/or compressor or other processing element). See, for example, FIGS. 6A-6B.
  iii. Filter manipulator 264 is arranged to store and manipulate filters. See, for example, FIGS. 7A-7D.
b. Filter manipulators such as 260, 262 and 264. Each may include movement modules (261, 263, 265 and 275)

and storage modules (272 and 270). i. Filter manipulator 260 is arranged to store and manipulate pre-used filters (including inserting the pre-used filters to a pool cleaning robot 100, providing and/or arranging filters to/within filter storage module 272, ejecting filters from a pool cleaning robot (see, arm 261 of FIGS. 6A and 6B). ii. Filter manipulator 262 is arranged to store and manipulate used-filters (extract from pool cleaning robot, direct used filter towards housing and/or compressor or other processing element). See, for example, FIGS. 6A-6B. iii. Filter manipulator 264 is arranged to store and manipulate filters. See, for example, FIGS. 7A-7D.

a. In-housing manipulator 711 for manipulating filters within housing 250. b. Filter manipulators such as 260, 262 and 264. Each may include movement modules (261, 263, 265 and 275) and storage modules (272 and 270). i. Filter manipulator 260 is arranged to store and manipulate pre-used filters (including inserting the pre-used filters to a pool cleaning robot 100, providing and/or arranging filters to/within filter storage module 272, ejecting filters from a pool cleaning robot (see, arm 261 of FIGS. 6A and 6B). ii. Filter manipulator 262 is arranged to store and manipulate used-filters (extract from pool cleaning robot, direct used filter towards housing and/or compressor or other processing element). See, for example, FIGS. 6A-6B. iii. Filter manipulator 264 is arranged to store and manipulate filters. See, for example, FIGS. 7A-7D.

The sensing and communication module 720 may include at least one out of weight sensor 721, ultrasonic transceiver 722, proximity sensor 723, cleanliness sensor 724 and communication unit 725. The sensors 721, 722, 723 are arranged to sense the location of a pool cleaning robot 100 and/or evaluate wherein the pool cleaning robot is positioned in a docking position in which it can be charged and/or receive or extract filters. Cleanliness filter 724 may sense the cleanliness of pre-used filters and/or used-filters. It may indicate that an extracted filter is clean enough to be used and cause the controller 740 to control a process of returning the used filter to the pool cleaning robot 100 via one of the filter manipulators. The communication unit 725 may be arranged to communicate with the pool cleaning robot or other devices in or outside the pool. It may include, for example radiation sources 241 and 242 of FIG. 1.

The power supply module 207 may include at least one of the following:
  a. Electrical cable 402 (FIG. 3A).
  b. Turbine 404 (FIG. 4B).
  c. Electrical generator 406 (FIG. 2B).
  d. Rechargeable power source 405.
  e. First contactless charging element (such as a coil) 210 (see FIG. 1).
  a. Electrical cable 402 (FIG. 3A). b. Turbine 404 (FIG. 4B). c. Electrical generator 406 (FIG. 2B). d. Rechargeable power source 405. e. First contactless charging element (such as a coil) 210 (see FIG. 1).

The underwater processing module 700 may include at least one of the following:
  a. Ejector 707 for ejecting used filters from the underwater station 200.
  b. Floater 709 for attaching or otherwise associating a used filter with floating materials (foam, inflated balloon).
  c. Compressor 701 and/or 265 (see FIGS. 6A-6B).
  d. Shredder 703.
  e. Sanitizer 705.
  a. Ejector 707 for ejecting used filters from the underwater station 200. b. Floater 709 for attaching or otherwise associating a used filter with floating materials (foam, inflated balloon). c. Compressor 701 and/or 265 (see FIGS. 6A-6B). d. Shredder 703. e. Sanitizer 705.

FIG. 20A illustrates a pool 300, a pool cleaning robot 100 and a pool fluid circulation system that includes drain 302, fluid pipes 304, filter 330, temperature control unit 320 and circulating pump 310 and tube 408. Any type of pool fluid circulation system can be utilized for the purposes of this invention. A pool can be regarded as a swimming pool, any type of pool or any type of vessel, container, enclosure that may contain fluid.

Any combination of any components of any pool cleaning robot illustrated in any of the figures may be provided.

Any reference to any pool cleaning robot is applied mutatis mutandis to a method for operating the pool cleaning robot.

Any combination of any components of any underwater systems can be provided.

Any reference to any underwater system is applied mutatis mutandis to a method for operating the pool cleaning robot.

FIG. 21 illustrates method 400 according to an embodiment of the invention.

Method 400 is autonomous operation. Method 400 includes step 410 of performing, by at least one of a pool cleaning robot and an underwater station, in an autonomous manner at least one out of pool cleaning robot filter replacement and pool cleaning robot charging.

The term autonomous may mean without human intervention. The pool cleaning robot charging is applied on a pool cleaning robot that is not constantly connected to a cord that extends outside the pool and constantly supplies to the pool cleaning robot electrical energy or supplied to the pool cleaning robot a constant a flow of fluid.

For example, executing the process at least partially illustrated in any one of FIGS. 1, 2A, 2B, 2C, 3A, 3B, 4A, 4B may amount to performing in an autonomous manner a pool cleaning robot charging.

Yet for another example, executing the process at least partially illustrated in any one of FIGS. 6A, 6B, 7A, 7B, 7C, 7D, 8 and 12 may amount to performing in an autonomous manner a pool cleaning robot filter replacement.

FIG. 22 illustrates method 500 according to an embodiment of the invention.

Method 500 includes stage 510 of filtering fluid by a pool cleaning robot by using a filter that fulfils at least one of the following: (i) it has a filter core that is rotated by a filter core rotator when the filter applied a filtering operation, (ii) is positioned in a filtering position while at least one other filter of the pool cleaning robot is positioned within the pool cleaning robot in a non-filtering position, (iii) is positioned in a filtering position when the pool cleaning robot and by a filter manipulator.

For example, the filtering can be executed by any one of the filters illustrated in FIGS. 5A, 5C, 6A, 6B, 7A, 7B, 7C, 7D, 8, 9, 10, 11A, 11B, 12, 13A, 13B, 16A, 16B, 17A-17F.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Those skilled in the art to which this invention pertains will readily appreciate that numerous changes, variations and modifications can be made without departing from the scope of the invention mutatis mutandis.

I claim:

1. A pool cleaning robot comprising:
    a drive motor;
    an impeller;
    an impeller motor that is configured to rotate the impeller;
       wherein the impeller, once rotated at a first rotational direction, is configured to induce fluid to flow through the pool cleaning robot;
    a filter for filtering fluid that flows through the pool cleaning robot; and
    wherein the filter and the impeller are detachably coupled to one or more elements of the pool cleaning robot, and are configured to concurrently exit the pool cleaning robot while the impeller motor remains coupled to the one or more elements of the pool cleaning robot.

2. The pool cleaning robot according to claim 1 wherein the impeller is configured to rotate about an axis that is located at a center of the filter.

3. The pool cleaning robot according to claim 1 wherein the filter comprises a cylindrical shaped filtering element that is partially surrounded by the filter.

4. The pool cleaning robot according to claim 1 wherein the filter comprises a cylindrical shaped filtering element that is fully surrounded by the filter enclosure.

5. The pool cleaning robot according to claim 4 wherein the impeller motor is configured to rotate the impeller about an axis and wherein the filter enclosure contacts the axis.

6. The pool cleaning robot according to claim 1 wherein the filter and the impeller are mechanically coupled to each other.

7. The pool cleaning robot according to claim 1 wherein the filter and the impeller are distant from each other.

8. The pool cleaning robot according to claim 1 wherein a top of the filter does not exceed a bottom of the impeller.

9. The pool cleaning robot according to claim 1 wherein a top of the impeller does not exceed a bottom of the filter.

10. The pool cleaning robot according to claim 1 comprising a first fluid opening and a second fluid opening; wherein the impeller, once rotated at the first rotational direction, is configured to induce the fluid to flow from the first fluid opening, through the pool cleaning robot, and to exit the pool cleaning robot from the second fluid opening.

11. The pool cleaning robot according to claim 1 comprising connecting elements for holding the filter within the pool cleaning robot; wherein the one or more elements comprise the connecting elements.

12. The pool cleaning robot according to claim 1 wherein the one or more elements of the pool cleaning robot comprise a part of a housing of the pool cleaning robot.

13. A method for operating a pool cleaning robot, the method comprises:
    rotating an impeller of the pool cleaning robot by an impeller motor of the pool cleaning robot at a first rotational direction thereby inducing, by the impeller, fluid to flow through the pool cleaning robot;
    filtering, by a filter of the pool cleaning robot, fluid that flows through the pool cleaning robot; and
    concurrently detaching the filter and the impeller from one or more elements of the pool cleaning robot thereby exiting the filter and the impeller from the pool cleaning robot while the impeller motor remains coupled to the one or more elements of the pool cleaning robot.

14. The method according to claim 13 wherein the one or more elements of the pool cleaning robot comprise a part of a housing of the pool cleaning robot.

15. The method according to claim 13 wherein the rotating comprises rotating the impeller about an axis that is located at a center of the filter.

16. The method according to claim 13 wherein the filter and the impeller are mechanically coupled to each other.

17. The method according to claim 13 wherein the filter and the impeller are distant from each other.

18. The method according to claim 13 wherein a top of the filter does not exceed a bottom of the impeller.

19. The method according to claim 13 wherein a top of the impeller does not exceed a bottom of the filter.

20. The method according to claim 13 wherein the concurrently detaching the filter and the impeller from one or more elements of the pool cleaning robot comprises concurrently detaching the filter and the impeller from connecting elements of the pool cleaning robot that are for holding the filter within the pool cleaning robot.

* * * * *